United States Patent
Abbaszadeh

(10) Patent No.: US 10,772,361 B2
(45) Date of Patent: Sep. 15, 2020

(54) PUMPING/NURSING BRA

(71) Applicant: Simple Wishes LLC, Dallas, TX (US)

(72) Inventor: Debra Abbaszadeh, San Francisco, CA (US)

(73) Assignee: Simple Wishes, LLC, Dallas, TX (US)

( * ) Notice: Subject to any disclaimer, the term of this patent is extended or adjusted under 35 U.S.C. 154(b) by 258 days.

(21) Appl. No.: 15/872,360

(22) Filed: Jan. 16, 2018

(65) Prior Publication Data

US 2018/0132542 A1     May 17, 2018

Related U.S. Application Data

(63) Continuation of application No. PCT/US2016/043326, filed on Jul. 21, 2016.

(60) Provisional application No. 62/196,080, filed on Jul. 23, 2015.

(51) Int. Cl.
    *A41C 3/04*        (2006.01)
    *A61M 1/06*        (2006.01)
    *A41C 3/14*        (2006.01)

(52) U.S. Cl.
    CPC ............... *A41C 3/04* (2013.01); *A41C 3/144* (2013.01); *A61M 1/062* (2014.02); *A61M 2209/088* (2013.01)

(58) Field of Classification Search
    CPC ......... A41C 3/04; A41C 3/144; A41C 3/0021; A41C 3/0057
    USPC ................................... 450/36, 30–33; 2/104
See application file for complete search history.

(56) References Cited

U.S. PATENT DOCUMENTS

| | | |
|---|---|---|
| 623,413 A | 4/1899 | Murray |
| 949,414 A | 2/1910 | Cunningham |
| 2,305,051 A | 11/1940 | Witkower |
| 2,436,430 A | 2/1948 | Hart |
| 2,492,862 A | 12/1949 | Harvey |
| 2,522,010 A | 9/1950 | Woodruff |
| 2,585,338 A | 2/1952 | Meares |

(Continued)

FOREIGN PATENT DOCUMENTS

| | | |
|---|---|---|
| AU | 2011100651 A4 | 7/2011 |
| CN | 201479956 U | 5/2010 |

(Continued)

OTHER PUBLICATIONS

Office Action for U.S. Appl. No. 12/453,073, dated Sep. 23, 2011, 11 pages.

(Continued)

*Primary Examiner* — Gloria M Hale
(74) *Attorney, Agent, or Firm* — Cooley LLP

(57) ABSTRACT

A garment (e.g., a bra) can include an inner pumping panel with layers of material. A first portion of the layers of material of the inner pumping panel may be situated on a left side of the bra to cover a portion of the wearer's left breast and can be fastened together and define a first opening. A second portion of the layers of material of the inner pumping panel may be situated on a right side of the bra to cover a portion of the wearer's right breast, and can be fastened together and define a second opening. The first and second openings are each disposed at an oblique angle relative to a bottom edge of the bra and are sized and positioned so as to help support at least a portion of a breast pump disposable through the first and/or second opening.

35 Claims, 36 Drawing Sheets

(56) References Cited

U.S. PATENT DOCUMENTS

| | | | |
|---|---|---|---|
| 2,613,355 A | 10/1952 | Coleman | |
| 2,679,048 A | 5/1954 | Alberts | |
| 2,738,509 A | 3/1956 | Bauder | |
| 3,002,515 A | 10/1961 | Giogover | |
| 4,335,728 A | 6/1982 | Fildan | |
| 4,640,287 A | 2/1987 | Anderson et al. | |
| 4,648,404 A | 3/1987 | Clark | |
| 4,878,879 A | 11/1989 | Kunstadter | |
| 4,911,677 A * | 3/1990 | White | A41C 3/04 2/104 |
| 5,098,330 A * | 3/1992 | Greenberg | A41C 3/10 450/31 |
| 5,334,082 A * | 8/1994 | Barker | A41C 3/10 2/247 |
| 5,341,514 A | 8/1994 | Dale | |
| 5,380,238 A | 1/1995 | Crew-Gee | |
| 5,395,280 A * | 3/1995 | Greenberg | A41C 3/148 2/247 |
| 5,514,166 A | 5/1996 | Silver et al. | |
| 5,575,768 A | 11/1996 | Lockridge et al. | |
| 5,616,125 A | 4/1997 | Jelks | |
| 5,690,537 A * | 11/1997 | Kalmus | A41C 3/10 2/267 |
| 6,004,186 A | 12/1999 | Penny | |
| 6,027,396 A | 2/2000 | Yonchar | |
| 6,086,451 A * | 7/2000 | Fernandes | A41F 15/002 2/67 |
| 6,227,936 B1 | 5/2001 | Mendoza | |
| 6,247,996 B1 | 6/2001 | Fields | |
| 6,319,092 B1 | 11/2001 | Leyhe et al. | |
| 6,438,758 B1 | 8/2002 | Burkard et al. | |
| 6,440,100 B1 | 8/2002 | Prentiss | |
| 6,705,920 B1 | 3/2004 | Engel | |
| 6,854,132 B1 * | 2/2005 | Polzin | A41C 3/04 2/104 |
| 6,866,558 B2 | 3/2005 | Luciano et al. | |
| 6,887,217 B1 | 5/2005 | Logan | |
| 6,974,361 B2 | 12/2005 | Cravaack et al. | |
| 7,232,359 B1 | 6/2007 | Richardson | |
| 7,306,505 B2 * | 12/2007 | Barbour | A41C 3/0057 2/DIG. 2 |
| 7,507,141 B2 * | 3/2009 | Ward | A41F 15/002 2/69 |
| 7,591,706 B2 * | 9/2009 | Barbour | A41C 3/0057 2/106 |
| 8,192,247 B2 * | 6/2012 | Abbaszadeh | A41C 3/04 2/104 |
| 8,323,070 B2 * | 12/2012 | Abbaszadeh | A41C 3/04 450/36 |
| 8,523,629 B2 * | 9/2013 | Pundyk | A41C 3/0021 450/30 |
| 9,167,855 B2 * | 10/2015 | Abbaszadeh | A41C 3/04 |
| 9,498,005 B2 * | 11/2016 | Abbaszadeh | A41C 3/04 |
| 9,872,524 B2 * | 1/2018 | Abbaszadeh | A61M 1/062 |
| 10,212,972 B2 * | 2/2019 | Abbaszadeh | A61M 1/062 |
| 10,420,377 B2 * | 9/2019 | Abbaszadeh | A61M 1/06 |
| 10,420,378 B2 | 9/2019 | Kosak | |
| 10,426,203 B2 | 10/2019 | Kosak | |
| 2002/0062512 A1 * | 5/2002 | Gustafson | A41B 9/08 2/118 |
| 2003/0027491 A1 | 2/2003 | Cravaack et al. | |
| 2003/0167037 A1 | 9/2003 | Fialkoff | |
| 2003/0191433 A1 | 10/2003 | Prentiss | |
| 2003/0232573 A1 * | 12/2003 | Plew | A41C 3/00 450/86 |
| 2004/0016039 A1 | 1/2004 | Capri | |
| 2006/0025039 A1 * | 2/2006 | Barbour | A41C 3/0057 450/1 |
| 2006/0211336 A1 | 9/2006 | Brigham | |
| 2007/0161330 A1 | 7/2007 | Whitehead et al. | |
| 2008/0022434 A1 * | 1/2008 | Adelman | A41D 1/215 2/104 |
| 2008/0039781 A1 | 2/2008 | Bjorge | |
| 2008/0146118 A1 | 6/2008 | Solberg et al. | |
| 2008/0262420 A1 | 10/2008 | Dao et al. | |
| 2009/0286452 A1 | 11/2009 | Grayson | |
| 2010/0031418 A1 | 2/2010 | Op'T Hof | |
| 2010/0159801 A1 | 6/2010 | Abbaszadeh | |
| 2010/0159802 A1 | 6/2010 | Abbaszadeh | |
| 2011/0092134 A1 * | 4/2011 | Alva | A41C 3/04 450/36 |
| 2011/0237156 A1 | 9/2011 | Boonen et al. | |
| 2011/0314587 A1 | 12/2011 | Ritchie | |
| 2012/0184179 A1 | 7/2012 | Blitz | |
| 2013/0095727 A1 | 4/2013 | Abbaszadeh | |
| 2014/0087625 A1 * | 3/2014 | Ironi | A41C 3/04 450/36 |
| 2014/0220860 A1 * | 8/2014 | Alva | A41C 3/04 450/36 |
| 2014/0273737 A1 | 9/2014 | Cortese et al. | |
| 2014/0364035 A1 | 12/2014 | Abbaszadeh | |
| 2014/0364036 A1 | 12/2014 | Abbaszadeh | |
| 2016/0015092 A1 | 1/2016 | Abbaszadeh | |
| 2017/0265530 A1 | 9/2017 | Donlon et al. | |
| 2017/0280786 A1 | 10/2017 | Abbaszadeh | |
| 2017/0280787 A1 | 10/2017 | Burrell | |
| 2018/0064177 A1 | 3/2018 | Akerson et al. | |
| 2018/0064178 A1 | 3/2018 | Akerson et al. | |
| 2018/0206559 A1 | 7/2018 | Kosak | |
| 2018/0255840 A1 | 9/2018 | Abbaszadeh | |
| 2018/0352884 A1 | 12/2018 | Vanos | |
| 2019/0142078 A1 | 5/2019 | Kosak | |
| 2019/0289926 A1 | 9/2019 | Abbaszadeh | |

FOREIGN PATENT DOCUMENTS

| | | |
|---|---|---|
| EP | 2810573 | 8/2016 |
| FR | 881406 A | 4/1943 |
| FR | 919893 A | 3/1947 |
| GB | 2536541 A | 9/2016 |
| KR | 2011-0001216 | 2/2011 |
| WO | WO 2007/053073 | 5/2007 |
| WO | WO 2008/005713 | 1/2008 |
| WO | WO 2010/080122 | 7/2010 |
| WO | WO 2011/135092 | 11/2011 |

OTHER PUBLICATIONS

International Search Report and Written Opinion for International Application No. PCT/US2009/006618, dated Mar. 8, 2010, 9 pages.

Office Action for U.S. Appl. No. 12/585,829, dated Aug. 24, 2011, 10 pages.

Office Action for U.S. Appl. No. 13/692,204, dated Oct. 1, 2014, 9 pages.

Office Action for U.S. Appl. No. 13/692,204, dated Jul. 3, 2013, 6 pages.

Office Action for U.S. Appl. No. 13/692,204, dated Apr. 8, 2014, 6 pages.

Office Action for U.S. Appl. No. 14/867,979, dated Nov. 5, 2015, 8 pages.

Office Action for U.S. Appl. No. 14/867,979, dated Apr. 4, 2016, 6 pages.

Extended European Search Report for European Application No. 14171552.4, dated Sep. 9, 2014, 6 pages.

Office Action for European Application No. 14171552.4, dated Dec. 3, 2015, 4 pages.

Office Action for U.S. Appl. No. 14/172,812, dated Jun. 16, 2016, 8 pages.

First Office Action for Chinese Application No. 201410077245.4, dated Dec. 7, 2016, 31 pages.

Second Office Action for Chinese Application No. 201410077245.4, dated Oct. 30, 2017, 29 pages.

Third Office Action for Chinese Application No. 201410077245.4, dated Jul. 9, 2018, 34 pages.

Extended European Search Report for European Application No. 14171556.5, dated Sep. 10, 2014, 5 pages.

Office Action for U.S. Appl. No. 14/172,826, dated May 20, 2016, 8 pages.

(56) References Cited

OTHER PUBLICATIONS

Office Action for U.S. Appl. No. 14/172,826, dated Dec. 29, 2016, 5 pages.
Office Action for U.S. Appl. No. 14/172,826, dated Apr. 10, 2017, 15 pages.
Extended European Search Report for European Application No. 16179769.1, dated Feb. 10, 2017, 8 pages.
Office Action for U.S. Appl. No. 15/873,317, dated Jun. 29, 2018, 9 pages.
International Search Report and Written Opinion for International Application No. PCT/US2016/043326, dated Nov. 28, 2016, 19 pages.
International Search Report and Written Opinion for International Application No. PCT/US2018/014245, dated Jun. 12, 2018, 15 pages.
Nursing Bra Express, "Pump Up the Band Hands Free Nursing Bra," [online], [Retrieved on Mar. 2, 2013], [Retrieved from the Internet: URL: <http://www.nursingbraexpress.com/nursing-bras/pump-band-hands-free-nursing-bra>.
Office Action for U.S. Appl. No. 15/357,596, dated Dec. 31, 2018, 12 pages.
Fourth Office Action for Chinese Application No. 201410077245.4, dated Mar. 21, 2019, 27 pages.
Decision on Rejection for Chinese Application No. 201410077245.4, dated Aug. 5, 2019, 26 pages.
Office Action for U.S. Appl. No. 15/873,456, dated Mar. 21, 2019, 14 pages.
Office Action for U.S. Appl. No. 16/201,718, dated Mar. 21, 2019, 11 pages.

\* cited by examiner

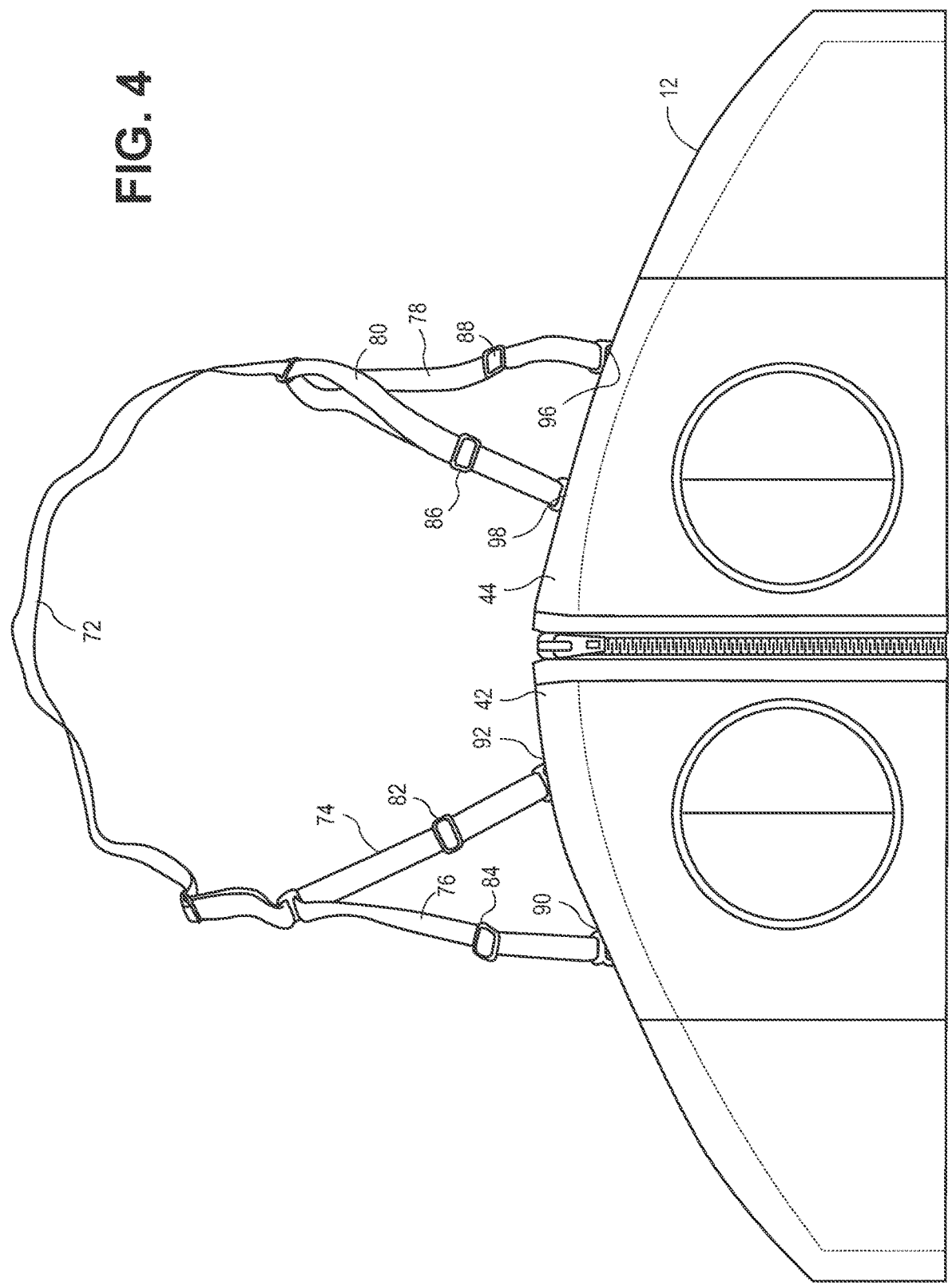

PUMPING/NURSING BRA

CROSS-REFERENCE TO RELATED APPLICATIONS

This application is a continuation of International Application No. PCT/US2016/043326, entitled "Pumping/Nursing Bra," filed Jul. 21, 2016, which claims priority to and the benefit of U.S. Provisional Application No. 62/196,080, entitled "Pumping/Nursing Bra," filed Jul. 23, 2015, each of the disclosures of which is hereby incorporated herein by reference in its entirety.

This application is related to U.S. Non-Provisional application Ser. No. 14/172,826, entitled "Pumping/Nursing Bra", filed Feb. 4, 2014, which claims priority to U.S. Provisional Application No. 61/832,592, filed on Jun. 7, 2013, and U.S. Non-Provisional application Ser. No. 14/172,812, entitled "Pumping/Nursing Bra", filed Feb. 4, 2014, which also claims priority to U.S. Provisional Application No. 61/832,592, filed on Jun. 7, 2013, the disclosures of which are hereby incorporated herein by reference in their entirety.

BACKGROUND

Embodiments described herein relate to a bra that can provide support to a breast pumping device while the wearer of the bra is pumping breast milk using the breast pumping device.

A breast pump may be used to express milk from a breast. Implementations of breast pumps have a pump body to express the milk and a milk container to receive the milk. The pump body of a breast pump may have a breast shield or a flange having a funnel shape with a cup portion that fits over at least a portion of a breast.

A let-down cushion or let-down massage cushion of a breast pump may fit between a breast shield or a flange of a pump body of the breast pump and a breast. The let-down cushion may fit within the breast shield or flange and have an edge that folds over an edge of the breast shield or the flange of the pump body. The let-down cushion may flex in and out to massage the areola of a breast to help stimulate milk flow. A seal may be formed between the let-down cushion and a breast to create suction and encourage breast milk expression.

To use a breast pump, a user manually holds the breast flange, shield, or pump body over a breast. While using the breast pump, the wearer is not able to use their hands for other tasks. It may be desirable to express milk from both breasts simultaneously, but doing so, requires the user to hold both breast pump bodies against oneself and is both awkward and does not allow the user to do other tasks. As such, garments that assist in supporting the breast pump body for milk expression are needed to allow a wearer to use their hands for other tasks during milk expression with a breast pump.

SUMMARY

Embodiments for garments, or bras, are provided with an inner pumping panel that includes layers of material and an exterior panel that includes first and second panels. A first portion of the layers of material in the inner pumping panel are situated on a left side of the bra to cover a portion of the wearer's left breast and the first portion of layers are fastened together to provide a first opening therebetween. Additionally, a second portion of the layers of material of the inner pumping panel are situated on a right side of the bra to cover a portion of the wearer's right breast, and the second portion of the layers are fastened together to provide a second opening therebetween.

Embodiments of garments, or bras, disclosed herein may include an inner pumping panel including a first covering for covering a portion of a wearer's first breast. The first covering includes a first portion of a center layer of material that at least partially overlaps a first layer of material. The first layer of material and the first portion of the center layer of material are fastened together in such a manner to define/provide a first opening therebetween. In some embodiments, the bra may also include a second covering for covering a portion of a wearer's second breast, the second covering can include a second portion of the center layer of material that at least partially overlaps a second layer of material, and the second layer of material and the second portion of the center layer of material can be fastened together in such a manner to define/provide a second opening therebetween.

A garment (e.g., a bra) described herein can include an inner pumping panel with layers of material. A first portion of the layers of material of the inner pumping panel may be situated on a left side of the bra to cover a portion of the wearer's left breast and can be fastened together such that at least a portion of the layers of material overlap and define a first opening. A second portion of the layers of material of the inner pumping panel may be situated on a right side of the bra to cover a portion of the wearer's right breast, and can be fastened together such that at least a portion of the layers of material overlap and define a second opening. The first and second openings are each disposed at an oblique angle relative to a bottom edge of the bra and are sized and positioned so as to help support at least a portion of a breast pump disposable through the first and/or second opening.

BRIEF DESCRIPTION OF THE DRAWINGS

FIG. 4 is a front view of a garment, according to another embodiment.

DETAILED DESCRIPTION

Figure 1A:
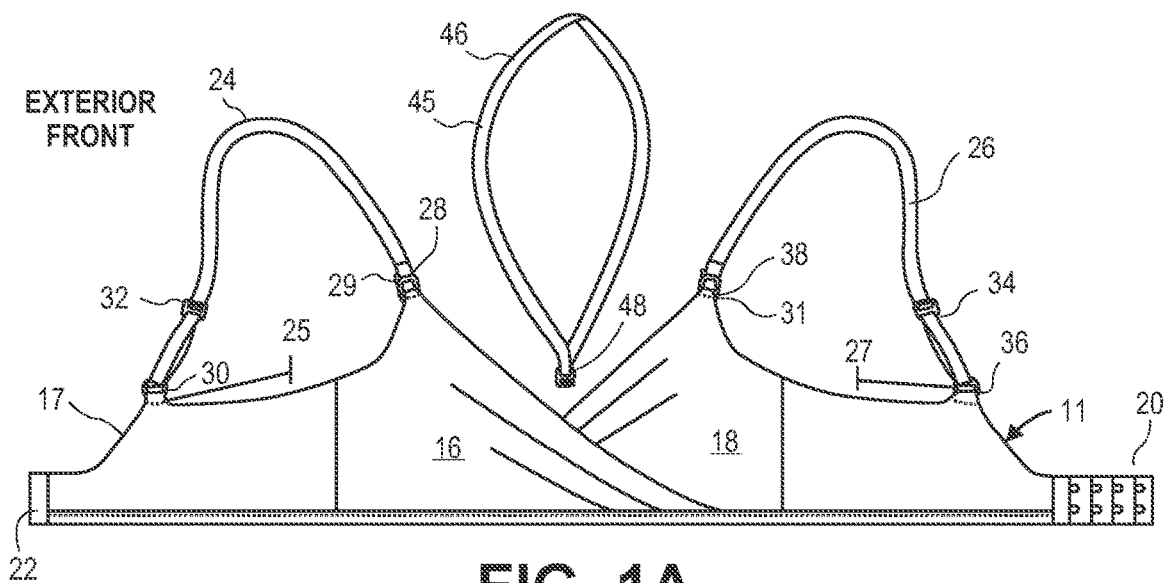
FIG. 1A is a front view of a garment, according to an embodiment.

Apparatuses, articles, processes for manufacture, garments, bustiers, breast pumping bras, and nursing bras that provide support to a wearer and/or at least a portion of a breast pump to aid with milk expression using a breast pump are described herein. For example, a garment, such as a bra, a tank top, a night gown, or a bustier, may provide support for the weight of a breast pump body, milk container, and/or a wearer's breast, help secure the breast pump body in place, and/or stabilize the breast pump body for milk expression. Various embodiments may provide support to aid with creation of a tight seal between the wearer's breast and at least a portion of a breast pump body for milk expression (e.g., a breast shield and/or a let-down cushion of a breast pump body). The wearer of the garment may be able to pump breast milk without having to manually hold the breast pump body against themselves.

Garments in accordance with some embodiments may have openings formed/defined between layers of material that are fastened together and/or to panels of the garment to provide openings for access to a wearer's breasts. In particular, the garment may have an inner panel (e.g., a pumping panel) having two openings providing access to the wearer's breasts that are formed between respective sets of layers of material. The layers of material can be coupled together such that at least a portion of the layers of material overlap each other, or alternatively can be coupled together in an abutting or edge-to-edge relationship. In some embodiments, the layers of material can be coupled together such that a portion of the layers overlap each other and a portion of the layers are coupled together in an abutting or edge-to-edge manner. Each opening is between the corresponding set of layers of material and the layers of material are fastened together in such a manner to define/provide the respective opening.

In some embodiments, the garment may have an exterior surface of one or more panels of material that cover the inner panel. When the panels of material and the layers of material that cover an opening are moved, the wearer can insert a portion of the breast pump body through the opening, and the layers of material and/or the panels of material of the garment can aid in supporting the breast pump body and/or the wearer's breast. The materials used for the inner and the exterior panel may be a fabric capable of being stretched to allow for pushing the material out of the way to insert the pump body portion, and the fabric may have some elasticity to then fit snugly under and/or around the pump body portion for support and return to the panels original shape covering the inner panel. In some embodiments, the garment may have elastic edges to prevent the garment from slipping down as well as providing additional support for the wearer's breasts.

Some embodiments may have one or more loops of a material (e.g., elastic, fabric, etc.) attached to the garment. Each loop may be designed to secure a portion of a breast pump in place (e.g., a loop to hook or fit around a breast shield to aid in the support of the breast pump body and milk container for pumping milk).

Some embodiments may have adjustable straps that may be selectively attached to the garment. For example, the garment can have a top line on the garment with corresponding attachment mechanisms to those found on the strap thereby allowing the strap to be attached thereto. For example, the top line may be a piece of material (e.g., an elastic band) attached to an edge of a panel (e.g., an inner panel) and the corresponding attachment mechanisms may be sewn to the garment with stitching between the elastic band and the fabric of the garment. The one or more attachment mechanisms (e.g., corresponding attachment mechanisms to the attachment mechanisms found on the strap) may be sewn to the garment for selectively attaching a strap in one of multiple different positions to support a breast pump body.

By way of further example, a neck strap can optionally be used and may extend around the back of the wearer's neck and be attached to the top line of the garment. The garment (e.g., a top line of a pumping/nursing bra) may have one or more selective attachment mechanisms (e.g., loops or hooks allowing for attachment of the strap to the garment). A plurality of selective attachment mechanisms may be provided on the garment to provide a plurality of positions for the strap. Attachment mechanisms may be hooks that may be selectively attached to a loop (e.g., a fabric, metal, or plastic loop), snaps, buttons and button holes, ribbon ties, lace ties, string ties, and/or any other attachment mechanism that can be selectively attached or detached. For example, a wearer could use a ribbon, lace, heavy string, etc. that could be threaded through a loop on the topline and tied where the two ends join. There may be a single strap and/or multiple straps that extend from one area of the bra to another as opposed to fitting around the neck. For example, a single strap could attach at the front topline, extend over the shoulder and hook at the topline below the underarm or back.

Continuing with the example, the neck strap may have a single hook that can be attached to the garment or a plurality of hooks that may be attached to the garment. The neck strap may ensure that the garment remains in place during breast pumping, particularly when the breast pump bottle becomes heavier as the container, which is used with the breast pump to collect milk, fills with milk. For example, a neck strap may encircle the neck of the wearer and have at least one hook attached to the top line of the garment to ensure that the garment remains in place during the use of a breast pump with at least one of the wearer's breasts. The neck strap may be used with or without shoulder straps of the garment. In some embodiments, a neck strap can include a comfort strap portion that has a width that is greater than a width of a typical strap to provide further comfort to the user. For example, the comfort strap portion can extend around the user's neck. In some embodiments, the comfort strap portion of the neck strap can be padded and/or can be formed with a material to provide softer comfort to the user's neck. In some embodiments, the width of the comfort portion can vary. For example, the width can be tapered or narrower at the ends of the comfort portion than at a center of the comfort portion.

In some embodiments, a pocket or a channel may be provided on a shoulder strap that contains and/or houses a cord or a strap with a hook or an attachment piece to connect to another area of the garment. The cord may be elastic to allow for the cord to be stretched and/or the cord may be stored within the pocket or channel rolled up into a coil, so that the cord can be extended and retracted. The cord may also have a slider to lengthen and shorten the strap as needed.

In some embodiments, the garment can include openings or holes along a perimeter top edge of the garment and the fastening mechanisms of the straps can be received therein to couple the straps to the garment. Such an embodiment is described in more detail below with reference to specific embodiments.

Other objects and advantages of the present invention will become apparent from the following detailed description when viewed in conjunction with the accompanying drawings, which set forth certain embodiments of the invention. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

FIG. 1A depicts an exemplary garment in accordance with some embodiments of the invention. FIG. 1A illustrates an exterior front surface 17 of a garment 11 (e.g., a pumping/nursing bra). The exterior front surface 17 includes a first panel of a material 16 crossing in front of a second panel of material 18, and both of the panels 16 and 18 provide a cover over the inner panel 19 in a covered state. The material may be any type of fabric capable of being stretched to uncover the inner panel and having elasticity to return to its original shape, and/or fit snugly under and/or around a portion of a breast pump body to provide support. The garment 11 (and garment 12 described below) may be made from nylon/spandex blends, cottons, polyesters, mesh fabrics, sheer fabrics, opaque fabrics, and/or any other materials. In some embodiments, portions of the garment 11 (and garment 12) may be made from fabrics that are sheer, transparent, and/or allow for visibility to the wearer's body (e.g., nylon, mesh, or basket weave). In particular, the sheer fabric of the garment 11 (and garment 12) may allow the wearer to see what areas of her body are irritated from the pumping process, and massage the areas with the sheer, thinner fabric. The panels may consist of one or more pieces of material that are sewn together to form an exterior surface 17. The panel 16 may cross over panel 18 to provide a smooth covering over an inner panel 19. In other embodiments, panel 16 and 18 may be a single panel of material that covers the inner panel. The inner panel 19 may be referred to herein as a pumping panel because the inner panel is formed to provide openings for access to a breast and insertion of a portion of a breast pump body.

In some embodiments, finger holes may be provided on an area of the inner panel to allow for massage to aid in the milk extraction.

Figure 1B:
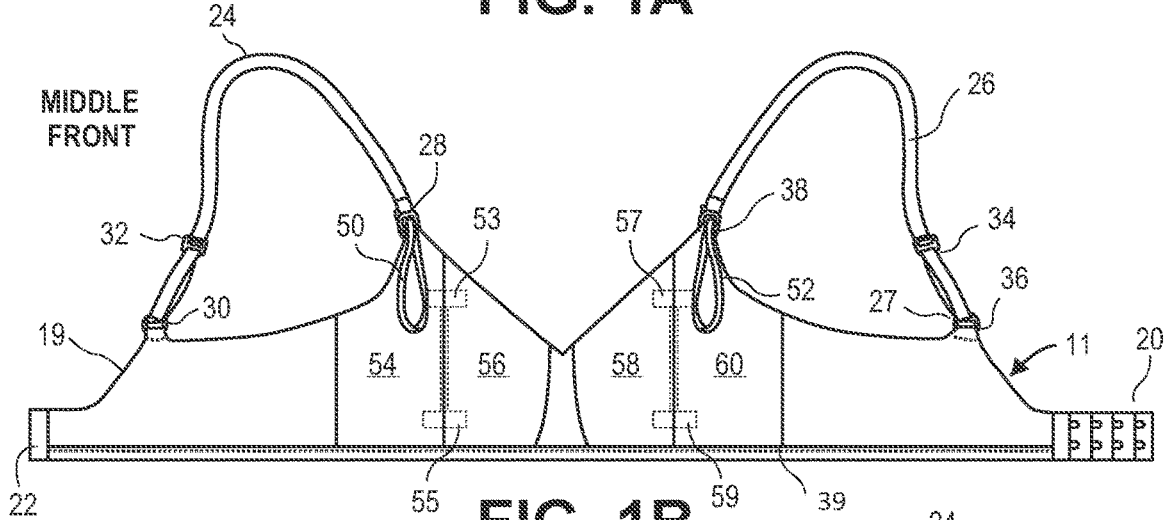
FIG. 1B is a front view of the garment of FIG. 1A with an exterior panel removed to show a middle layer of the garment.

FIG. 1B depicts an exemplary garment in accordance with some embodiments of the invention. FIG. 1B illustrates a front surface of the inner panel 19 (e.g., a pumping panel). The inner panel 19 may be covered by the panels 16 and/or 18 of the exterior front surface 17 in a covered state for the exterior front surface 17, or uncovered and accessible by moving and/or adjusting the panels 16 and/or 18 of the exterior front surface 17 in an uncovered state for the exterior surface 17. The inner panel 19 includes a first set of overlapping layers of material with a first layer of a material 54 and a second layer of a material 56, and a second set of overlapping layers with a third layer of a material 58 and a fourth layer of a material 60. A set of overlapping layers (e.g., layer 54 and layer 56) may be sewn to the garment 11 in such a way to overlap and form an opening and a line that is nearly perpendicular line to the bottom edge 39 of the garment 11, as shown. Those with skill in the art will recognize that an opening may be formed by sewing together layers of material that are at any angle to the bottom edge 39 of a garment, and embodiments are not limited to an opening that is perpendicular to the bottom edge 39.

The material used for the layers of material may be any type of fabric with elasticity to allow the layers to be stretched, moved, and return to their or nearly their original state. A layer of material (e.g., layers 54, 56, 58, or 60) each may be a single piece of material, multiple pieces of material, or a piece of material that has been folded over and sewn to the garment 11 to form a supportive layer of material. The layers of material on the inner panel 19 and panels of the exterior surface 17 may be created from different fabrics and materials.

Overlapping layers 54 and 56 can be moved to uncover, adjusted to separate, and/or allow one of the wearer's breasts to be accessible through the opening between the layers. Overlapping layers 58 and 60 may be likewise separated to uncover, adjust, and/or allow the other breast of the wearer to be accessible through the opening between the layers. The overlapping layers 54 and 56 may provide support for at least a portion of a breast pump body and/or a milk container when inserted through the opening formed between the overlapping layers. The panels of material 16 and/or 18 in the uncovered state may help to prevent the breast pump body and/or breast shields from slipping downward from the woman's breast by providing support beneath and/or around the breast pump body inserted through the opening. In some embodiments, the opening may be created between overlapping layers by stitching (e.g. bar tack stitching in a rectangular shape at 53 and 55) that fastens the layers of material together and leaves the opening between the stitching of the layers (e.g., bar tack stitching at 53 and 55). In some embodiments, the pump body may sit within the opening, and may keep the overlapping layers fastened together to fit around the pump body to keep it in place. Embodiments of the pumping panel 19 may b e provided with top rectangular shaped stitching panel 53 and a bottom rectangular shaped stitching panel 55 extending across a portion of the overlapping sections 54, 56 of the pumping panel 19. Similarly, a top rectangular stitching panel 57 and a bottom rectangular stitching panel 59 extend across a portion of the overlapping sections 58, 60 of the pump support panel 19. Although a rectangular shaped stitching is described, those with skill in the art will recognize that a variety of shapes and stitching may be used to fasten the layers together.

Figure 1C:
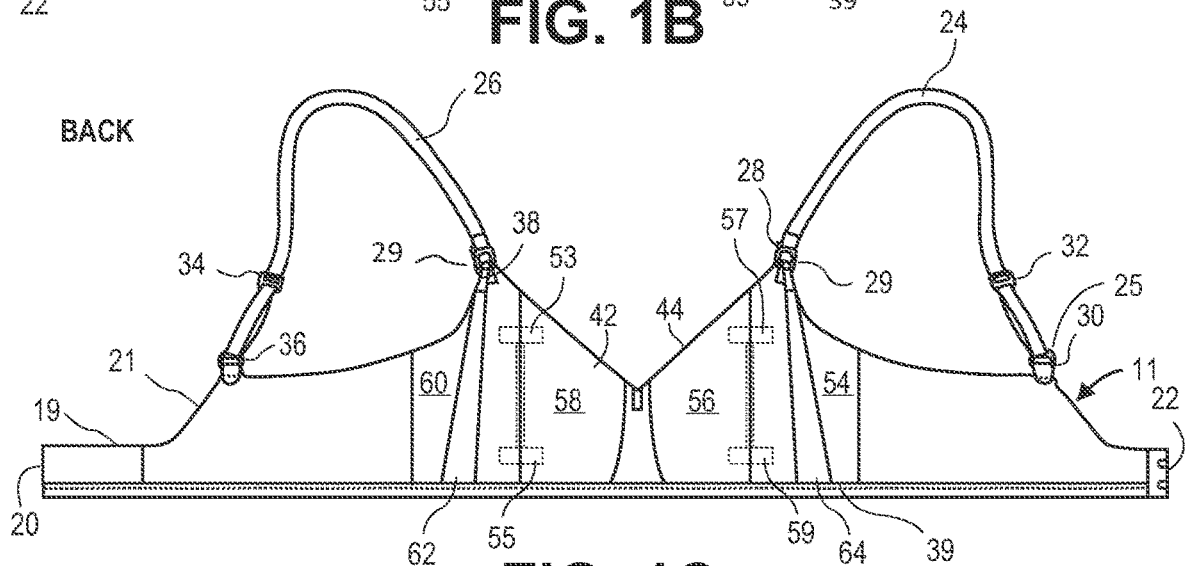
FIG. 1C is a back view of the garment of FIG. 1A.

FIG. 1C depicts an exemplary garment in accordance with some embodiments of the invention. FIG. 1C illustrates a rear surface 21 of the inner panel 19. A first shoulder strap 24 is provided at a first garment end 29 of the garment 11 with an attachment mechanism 28. The attachment mechanism 28 may have a first attachment end attached to a first stay end of a first fabric stay 64, and a second attachment end of the attachment mechanism 28 may be attached to a first garment end 29 of the inner panel 19 and one end of the front surface 17 and/or back surface 21 (e.g., panel 16), such as a sewn connection. Those with skill in the art will recognize that the attachment mechanism may be attached to the garment in a number of different ways, such as sewn in to the garment, sewn to an elastic band of the garment, slipped onto a strap, and/or any other method for securing the attachment mechanism.

Both first attachment end and second attachment end of the attachment mechanism 28 (e.g., a hook) are designed to be selectively attached to one another, connecting the first panel 16 to the first fabric stay 64 of the inner panel 19. The first fabric stay 64 may extend down with a second stay end of the first fabric stay 64 attached to the bottom edge 39 of the inner panel 19. A second strap end 25 of the first shoulder strap 24 may be attached to the garment 11 (e.g., a front surface 17, the panel 16, or the back surface 21) by an attachment mechanism 30 (e.g., a hook). Attachment mechanisms may be hooks, double hooks, snaps, buttons, and/or any other attachment mechanism for selective attachment. Alternatively, shoulder straps may cross in the back and first shoulder strap 24 may instead be secured to attachment mechanism 36 and second shoulder strap 26 may be secured to attachment mechanism 30.

A second shoulder strap 26 contains an attachment mechanism 38 (e.g., a hook) having a first attachment end 31 attached to a first stay end of a fabric stay 62. The second stay end of the second fabric stay 62 may be attached to the bottom edge 39 of the garment. A second attachment end of the attachment mechanism 38 is attached to one end of the inner panel 19 and one end of the panel 18. The first and second attachment ends of the attachment mechanism 38 are designed to attach to one another, connecting the second panel 18 to the pumping panel 19. The second shoulder strap 26 contains an attachment mechanism 36 (e.g., a hook member) connected to the garment 11.

A slide member 32 is provided on the first shoulder strap 24 and a slide member 34 is provided on the second shoulder strap 26. The slide members 32 and 34 are used to adjust the length of each of the shoulder straps 24, 26. Adjustable hook and eye closures 20, 22 are used to secure the garment 11 around the wearer's body. Those with skill in the art will recognize that other closures may be used to secure the garment 11 around the wearer's body, such as a zipper, a tie, VELCRO® closures, snaps, buttons, and/any other closure or attachment mechanism.

In some embodiments, double hook attachment mechanisms may be used as an alternative to the attachment mechanisms (e.g., hooks) 28, 38 shown in FIGS. 1A, 1B, and 1C. Double hook attachment mechanisms 20 will be described further in regards to FIGS. 15 and 16.

As shown in FIG. 1B, a first elastic loop 50 is attached to the first shoulder strap 24, fabric stay 64, and/or the inner panel 19. Additionally, a second elastic loop 52 is attached to the second shoulder strap 26, fabric stay 62, and/or the inner panel 19. The purpose of the loops 50, 52 is to fit around (e.g., hook) a portion of a breast pump body (e.g., the breast shield) and support the breast pump (e.g., a breast shield). Additional support may be helpful particularly when the breast pump container is filling with milk, as shown and described in further detail with FIG. 12 and FIG. 14. For example, the loops may be an elastic material that is sewn at both ends into the inner panel 19 of the garment 19. Those with skill in the art will recognize that loops may be attached to other parts of a garment 11 and similarly achieve the same purposes.

The loops may be attached to the garment 11 to hold or keep the breast pump body at a particular angle to ensure a seal is formed and/or not broken to allow for successful milk production. In some embodiments, the loop may have a slide or other mechanism to adjust the length of the loop surrounding the portion of the breast pump body. In other embodiments, the loop may have attachment mechanisms to open and close the loop around the breast pump body. The panels of the exterior surface 17 may cover the loops in a covered state.

The embodiment shown in FIG. 1A includes a neck strap 46 that is a single loop 45 joined together (e.g., sewn together) and that has an attachment mechanism 48 (e.g., a hook). The strap 46 may encircle the wearer's neck and then extend down from the wearer's neck toward the garment 11. The attachment mechanism 48 may be attached to a corresponding attachment mechanism (e.g., an opening to receive a hook) provided in a top line 42 and 44 of the garment 11 at a position (e.g., approximately at the center of the inner panel 19). The neck strap 46 may help to keep the garment 11 in place by providing additional stability when the wearer is pumping breast milk, particularly when a breast pump container is full of milk.

Figure 2A:
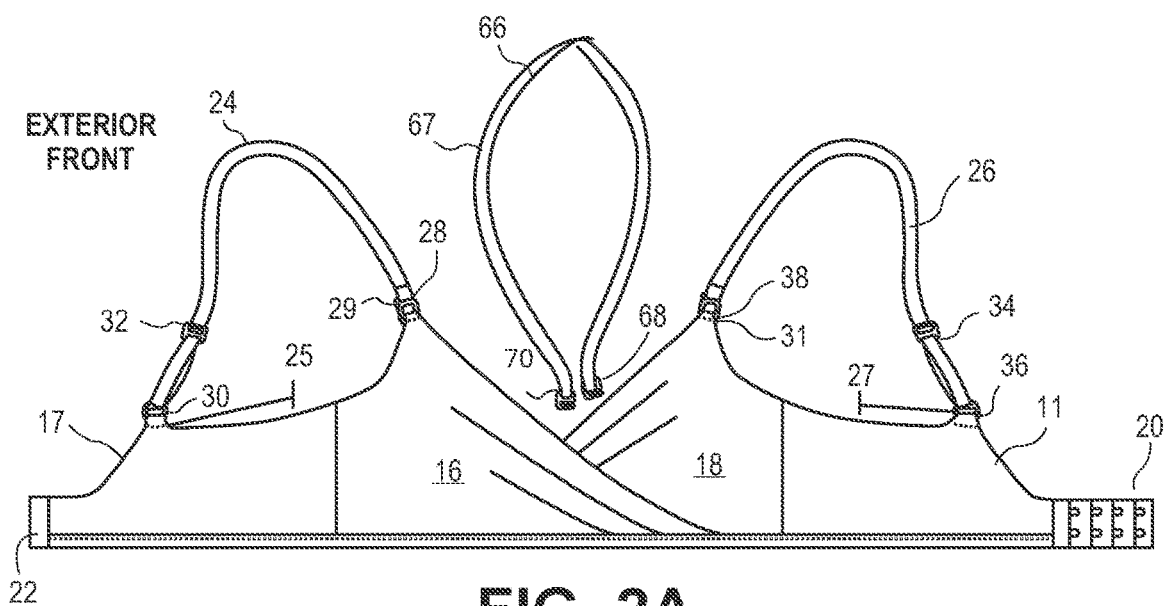
FIG. 2A is a front view of a garment of FIG. 1A with a different embodiment of a neck strap.
Figure 2B:
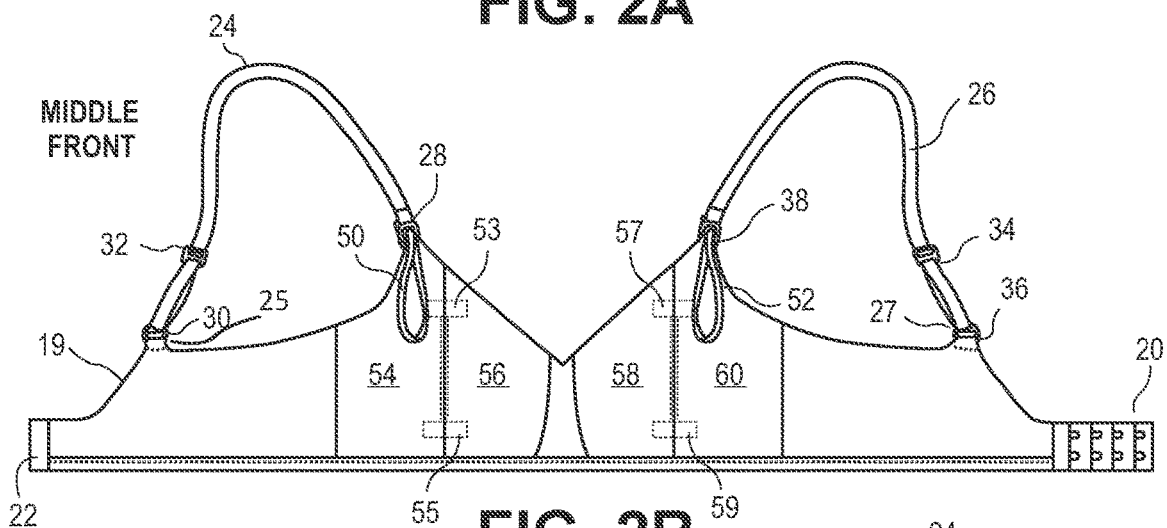
FIG. 2B is a front view of the garment of FIG. 2A with an exterior panel removed to show a middle layer of the garment.
Figure 2C:
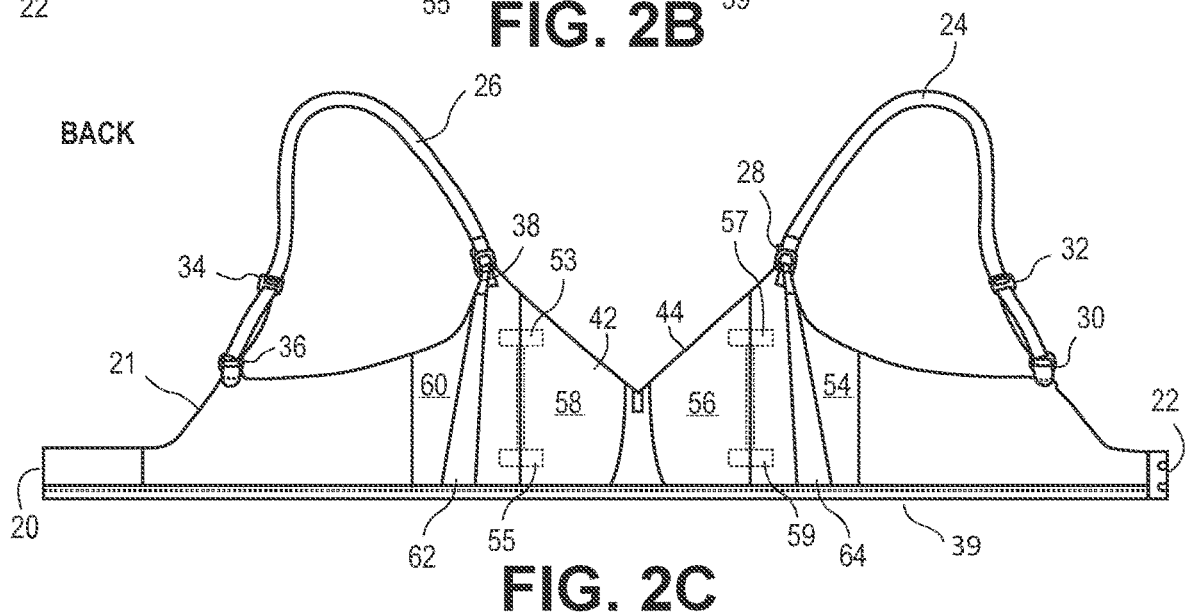
FIG. 2C is a rear view of the garment of FIG. 2A.

FIGS. 2A, 2B, and 2C illustrate an alternative embodiment that utilizes a strap 66 instead of the strap 46. Neck strap 66 may encircle the neck of the wearer with a single loop 67 and may have hooks 68, 70 at each end. Each of the hooks 68, 70 attach to the top line 42 and/or 44 (e.g., close to the center of the pumping panel 19 and/or on either side of the center). For the sake of description, two hook, loop attachments are described. However, those with skill in the art will recognize that a plurality of corresponding loops may be on a top line in a plurality of positions and capable of receiving a hook. Those with skill in the art will recognize that straps 46 and 66 may be secured to the garment 11 in a number of different locations on the top line 42 and/or 44 to provide stability and the positioning near the center is only provided as an example of such a location/position for the strap.

Figure 3A:
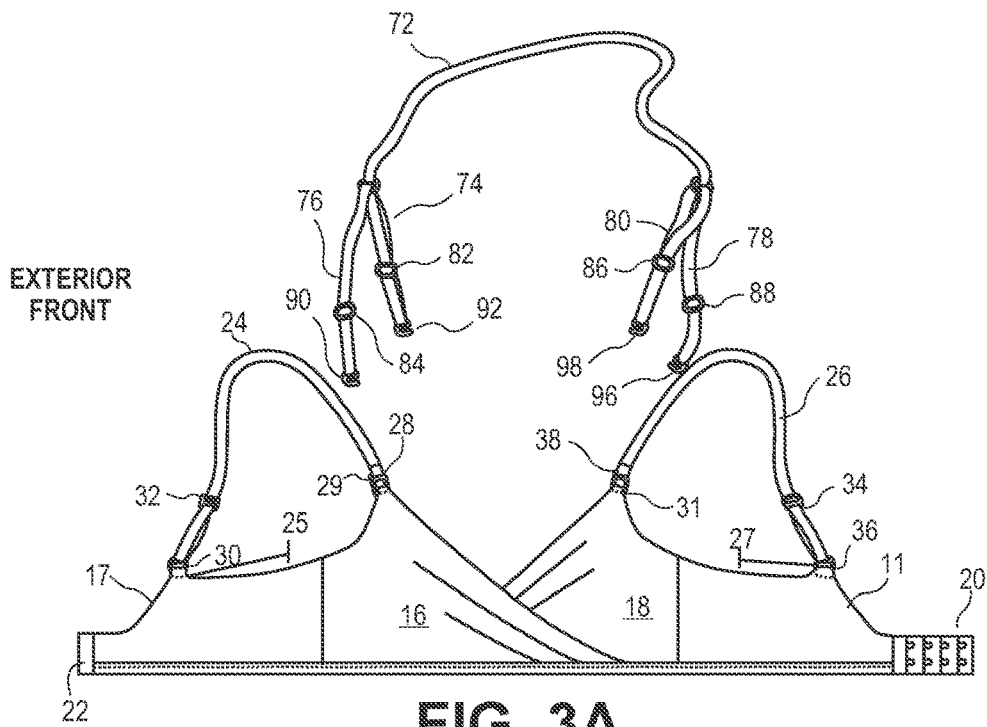
FIG. 3A is a front view of the garment of FIG. 1A with yet another different embodiment of a neck strap.
Figure 3B:
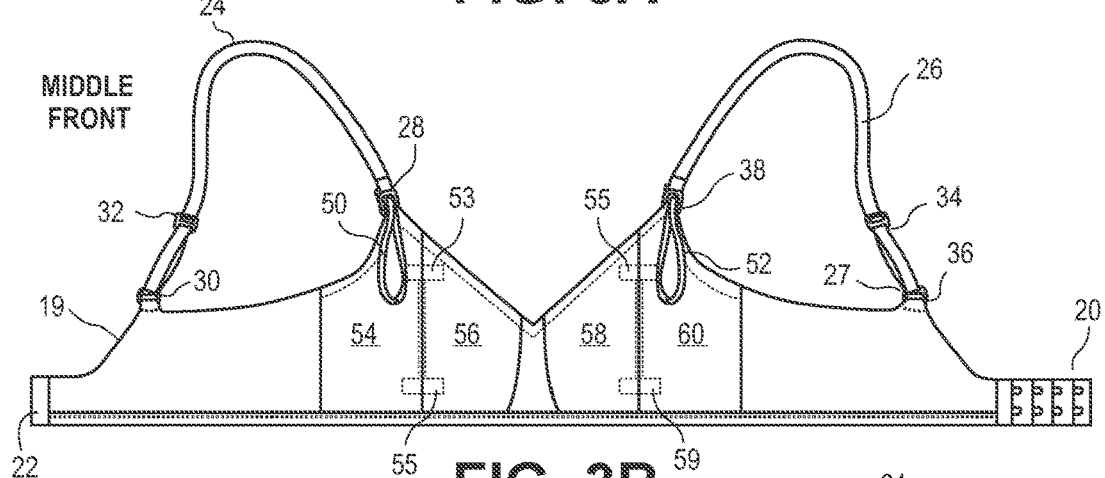
FIG. 3B is a front view of the garment of FIG. 3A with an exterior panel removed to show a middle layer of the garment.
Figure 3C:
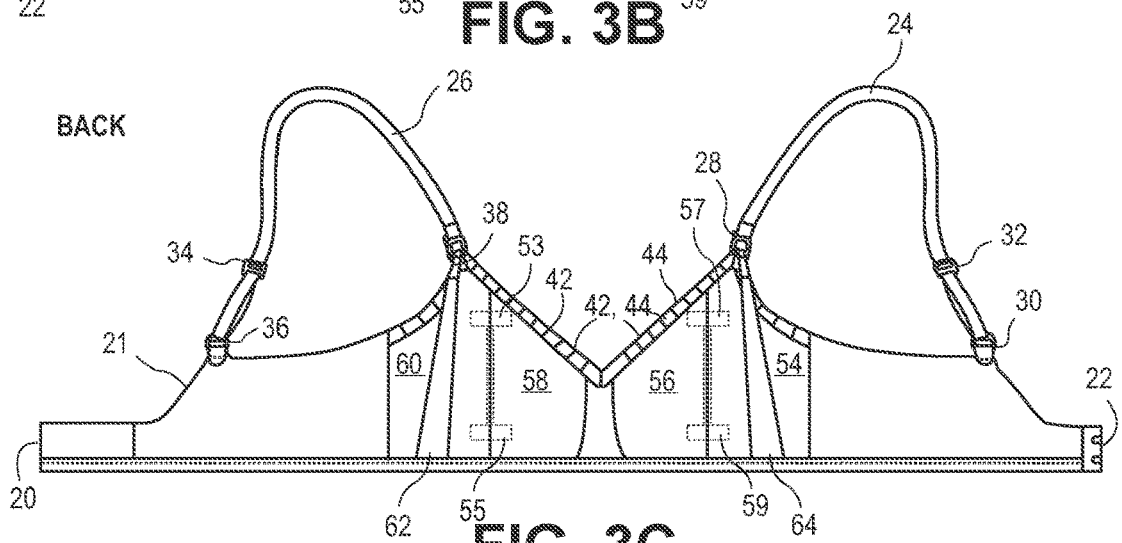
FIG. 3C is a rear view of the garment of FIG. 3A.

The embodiment shown in FIGS. 3A, 3B, and 3C employs a neck strap 72 in lieu of the straps 46, 66. The strap 72 contains extension sections 74, 76, 78, 80, each of which is provided with hooks 92, 90, 96, 98, respectively. Each of the hooks 90, 92, 96, 98 may be attached to the top line 42, 44. As can be appreciated, an increase in the number of extensions from the strap 72 and hooks secured to the garment 11 may offer greater stability and support for the breast pumps.

FIG. 4 shows an alternative garment that may be used with straps 46, 66, and/or 72. As shown, strap 72 may be attached to the top line 42, 44 of the garment 12. Adjustable slides 82, 84, 86, 88 allow for adjusting the length of the strap 72 to accommodate the wearer. Features of garment 12 are described in U.S. Pat. No. 8,192,247 filed Apr. 29, 2009, U.S. Pat. No. 8,323,070 filed Sep. 25, 2009, and U.S. patent application Ser. No. 13/692,204 filed Dec. 3, 2012, which are each incorporated by reference in their entirety. Garment 12 may have a covering for each opening that has pieces of material attached to a panel. A center panel may be selectively attached to left and right panels of the garment 12 (shown without the center panel).

Figure 5:
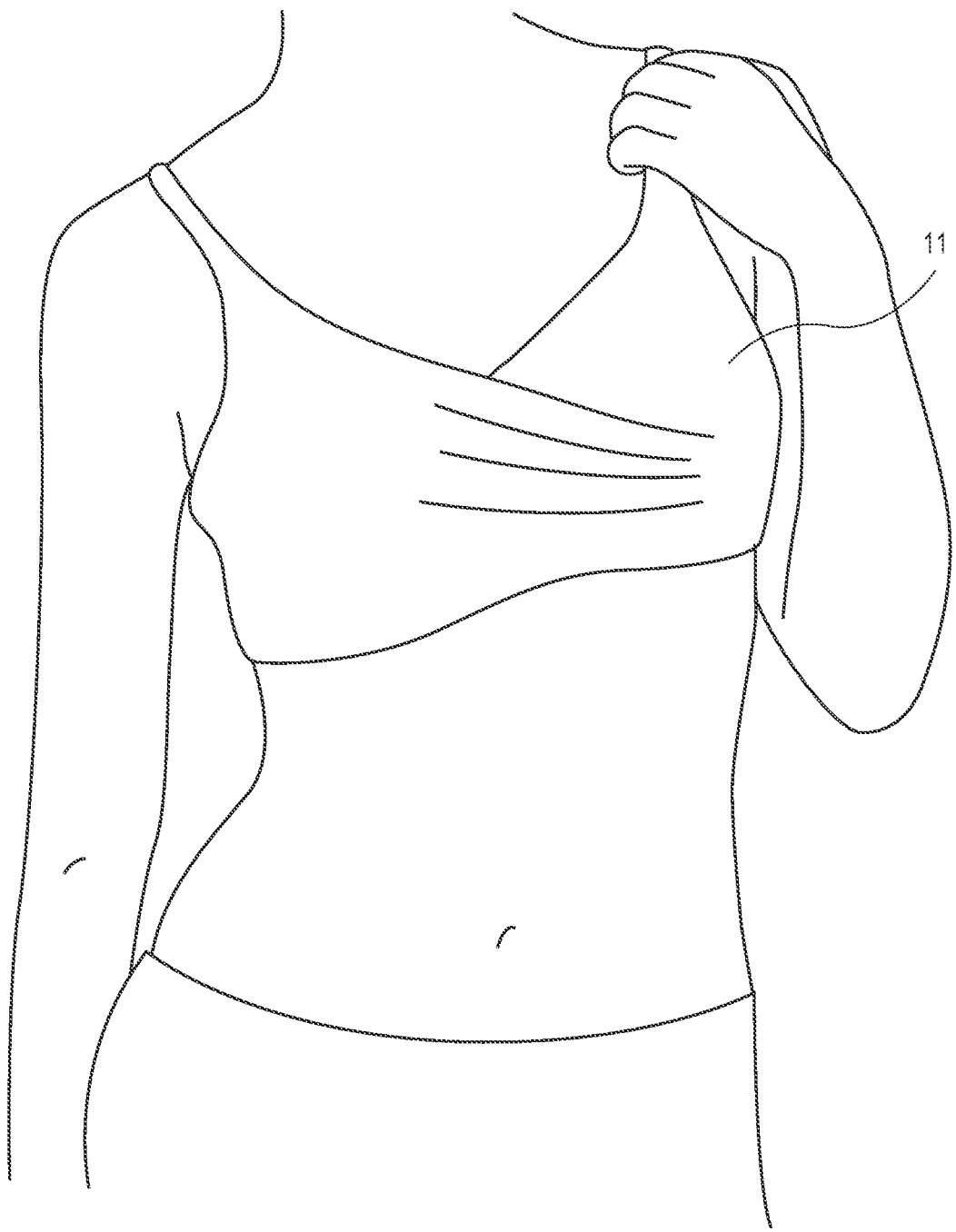
FIG. 5 is front perspective view of a garment according to an embodiment shown being worn by a wearer.
Figure 6:
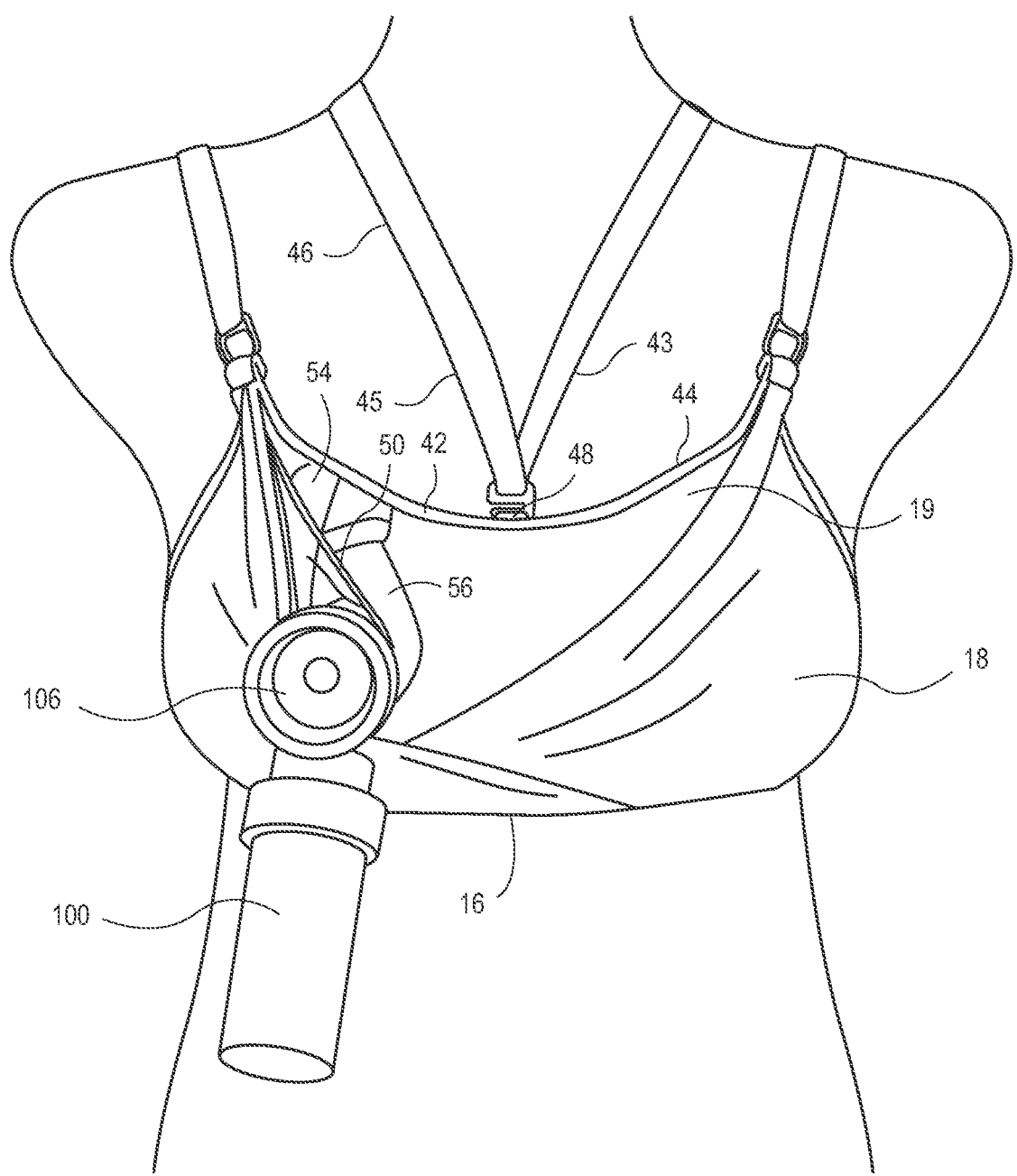
FIG. 6 is a front view of a garment according to an embodiment shown being worn by a wearer and using a breast pumping device.

FIGS. 5-13 illustrate the manner in which the garment 11 may be worn and used. The garment 11 may be worn as shown in FIG. 5 in a covered state for the exterior surface 17. As shown in FIG. 6, when breast milk pumping is initiated and/or further support is desired by the wearer, additional straps (e.g., 46, 66, or 72) may fit around the wearer's neck and be attached to the top line 42, 44 of the inner panel 19.

As shown in FIG. 6, the wearer may move the panel 16 slightly downward and/or to the wearer's right, allowing the woman to provide access/expose an opening between panels 54, 56 and to insert a breast shield of a breast pump body 106 between the panels 54, 56 and/or access the wearer's breast. A pumping container 100 may be used to capture expressed milk.

Figure 7:
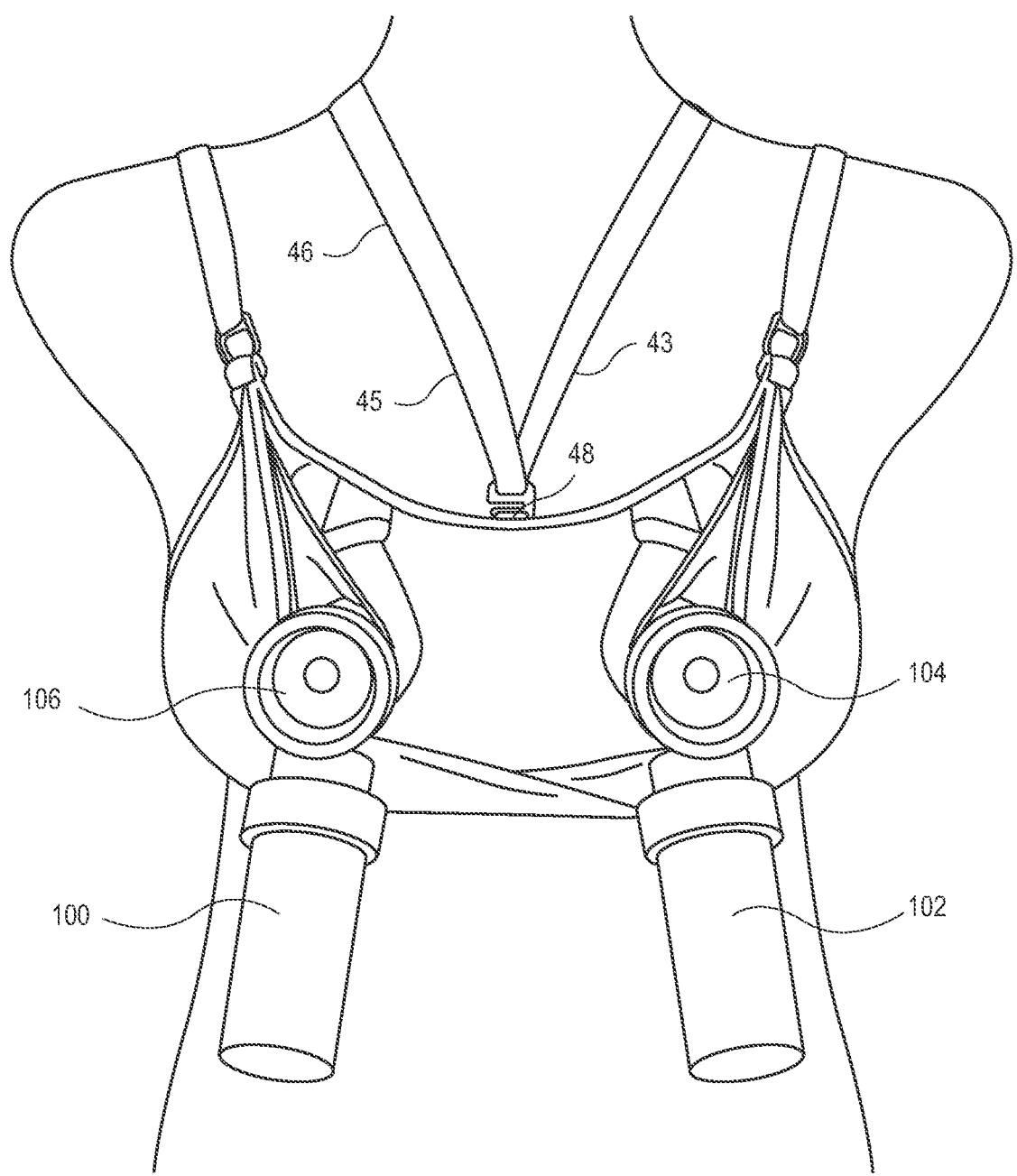
FIG. 7 is a front view of a garment according to an embodiment shown being worn by a wearer and using two breast pumping devices.

FIG. 7 illustrates the use of two pumping bottles 100, 102 connected to breast pumps with breast shields 106, 104 of the breast pump bodies, respectively. The breast shields 106 and 104 fit through the openings of the garment 11.

Figure 8:
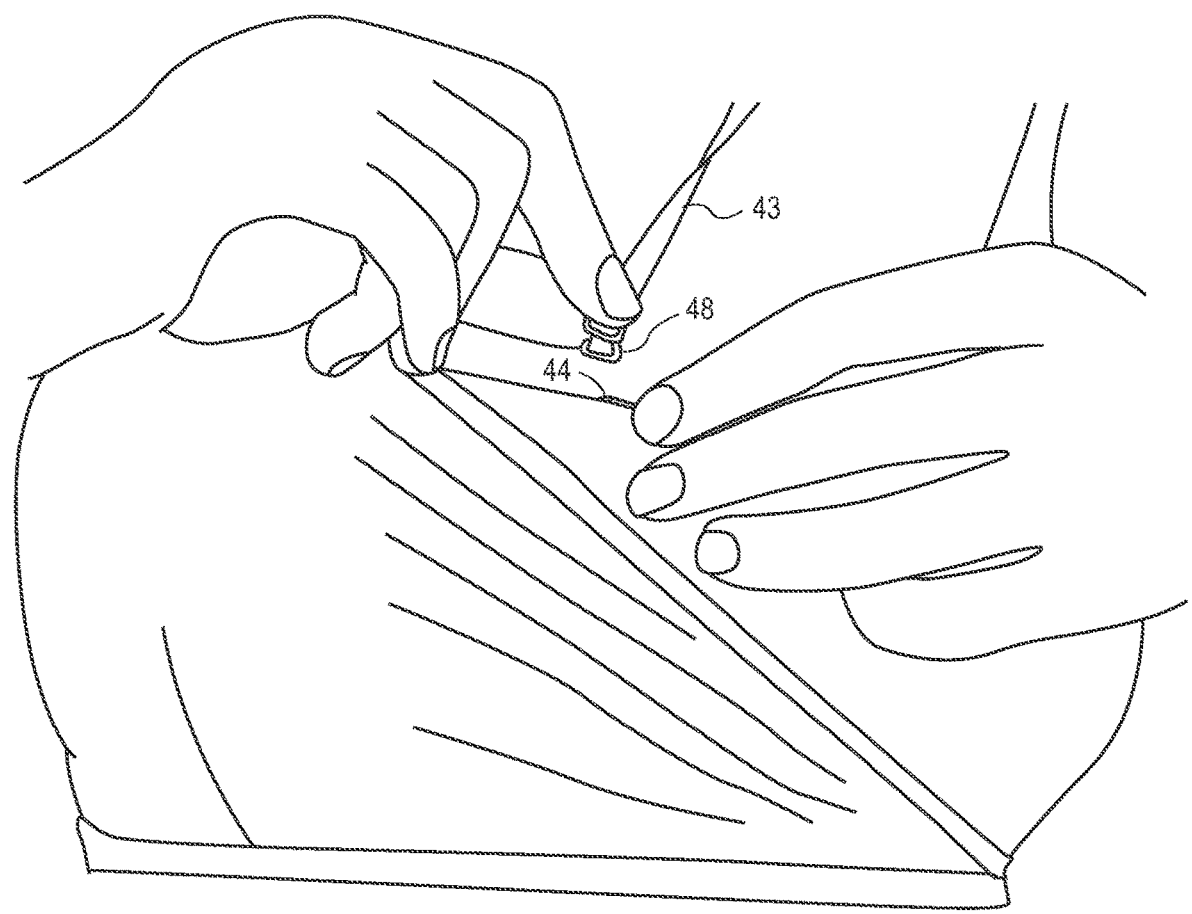
FIG. 8 illustrates the manner in which an attachment mechanism on a strap can be attached to a corresponding attachment mechanism provided on a body of the garment, according to an embodiment.

FIG. 8 shows the manner in which the attachment mechanism 48 (e.g., a hook) on the strap 46 may be attached to the corresponding attachment mechanism (e.g., a loop) provided within the top layer 42 and 44. For example, the corresponding attachment mechanism may be an elastic loop sewn in to the top line (e.g., a seam of the inner panel) that allows the hook attachment mechanism to be selectively attached.

Figure 9:
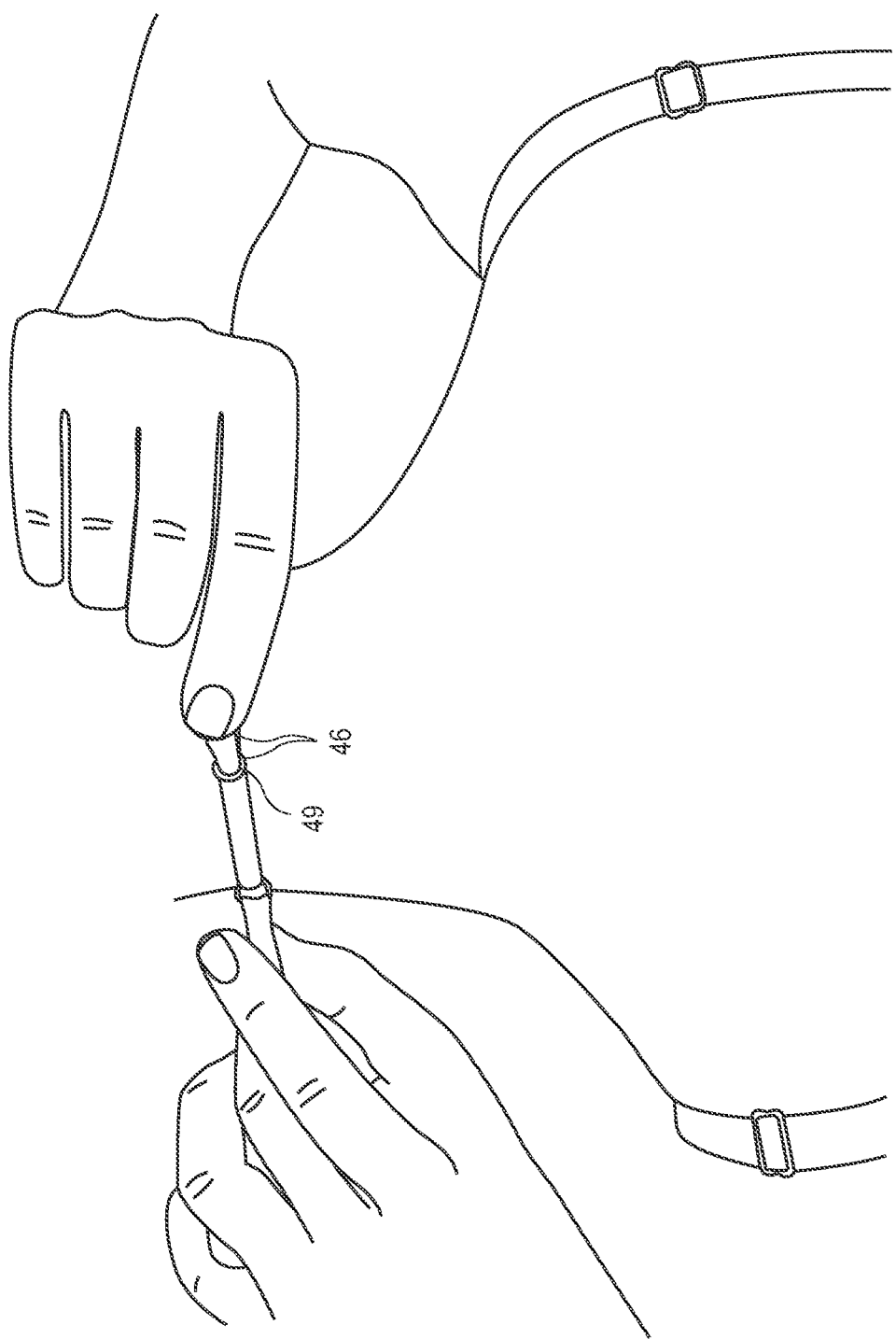
FIG. 9 illustrates the manner in which a neck strap encircles the neck of the wearer and a slide is provided to adjust the length of the strap, according to an embodiment.

FIG. 9 shows the manner in which the strap 46 encircles the neck of the wearer and a slide 49 is provided to adjust the length of the strap 46.

Figure 10:
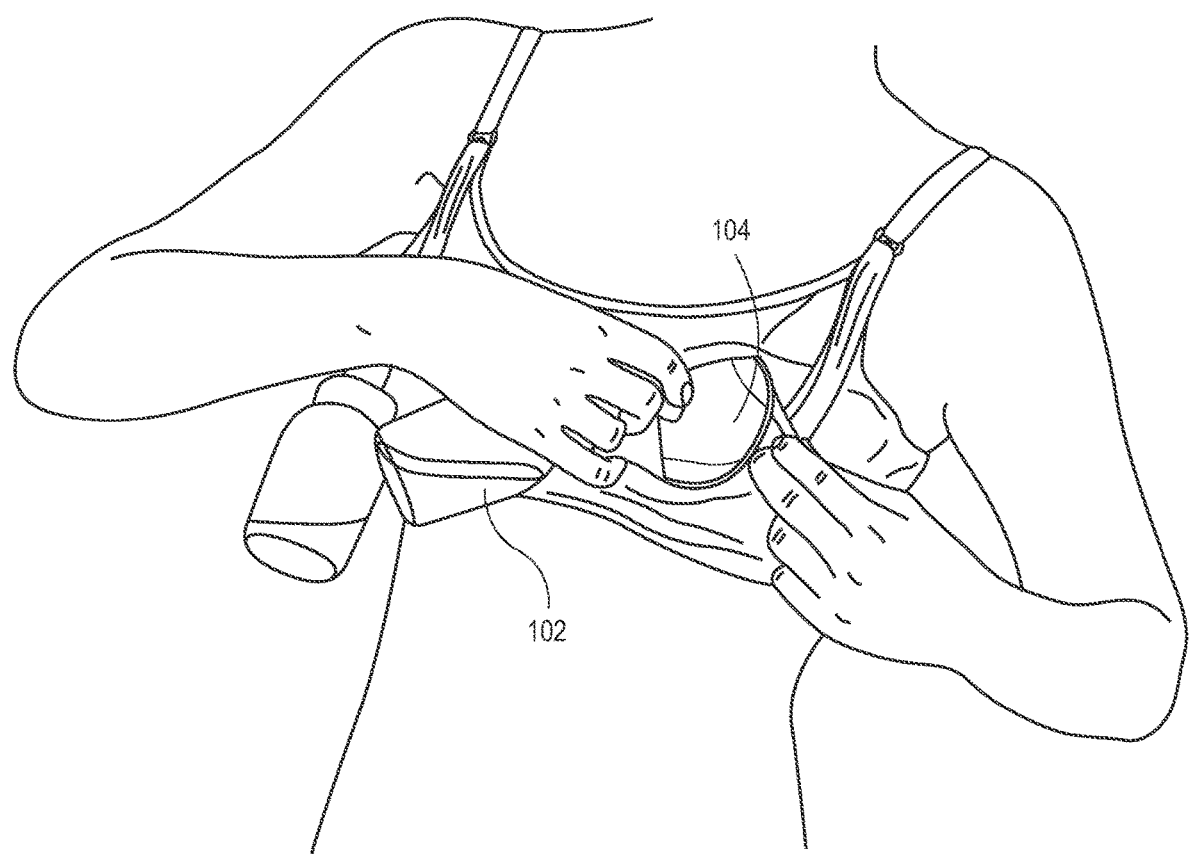
FIGS. 10-12 illustrate the manner in which a breast shield may be inserted through an opening of an inner panel of a garment, according to an embodiment.
Figure 11:
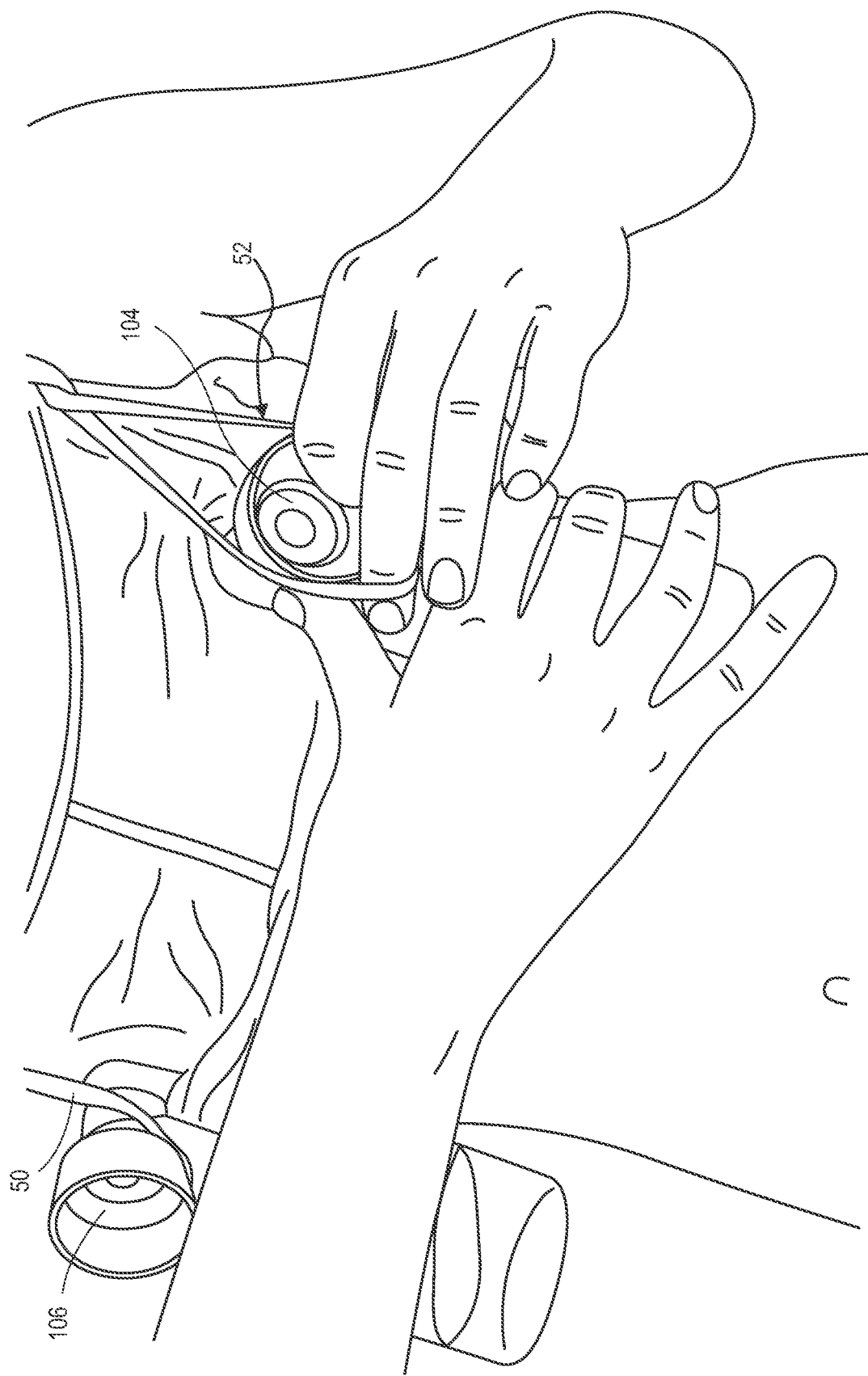
Figure 12:
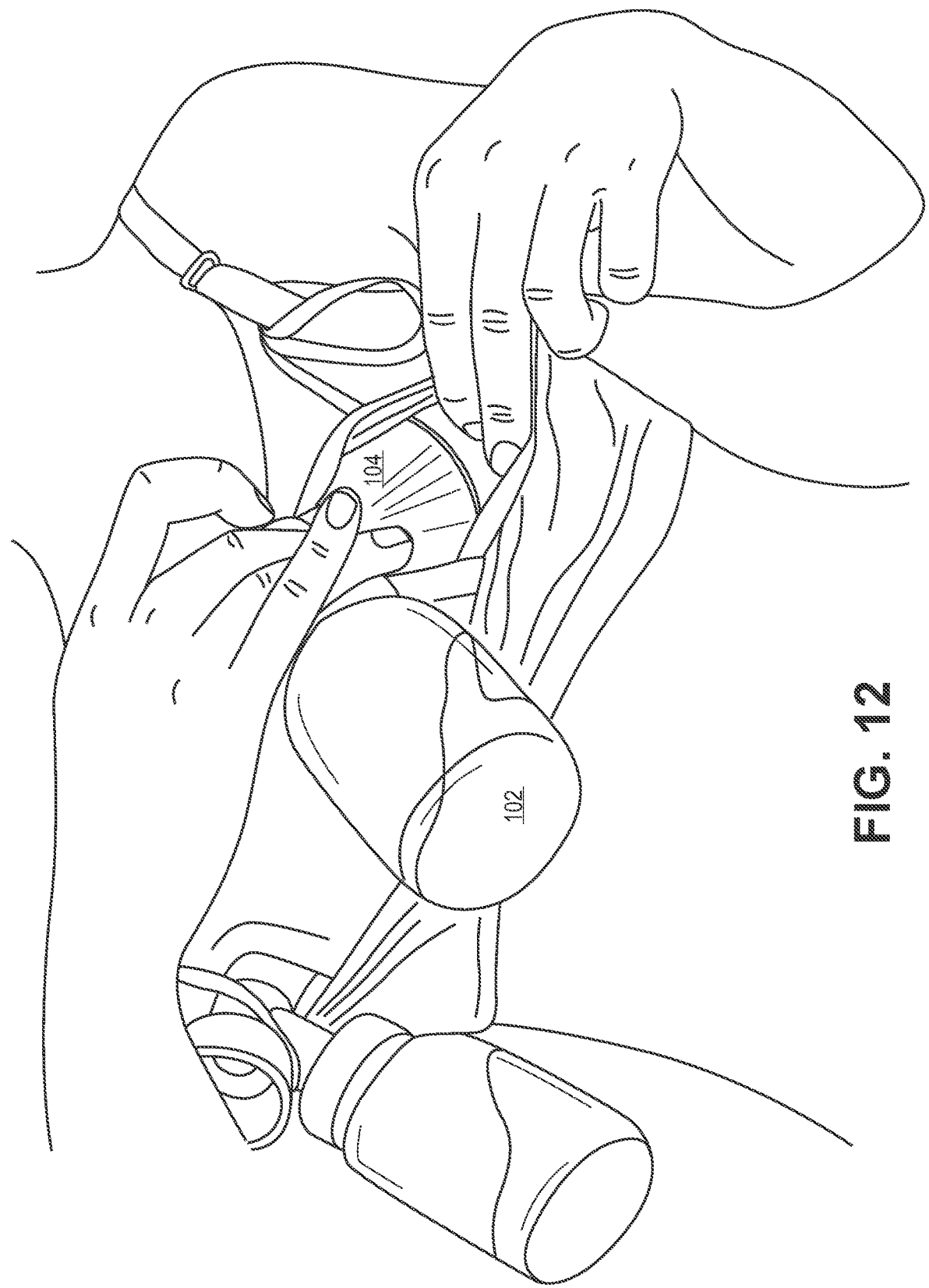
Figure 14:
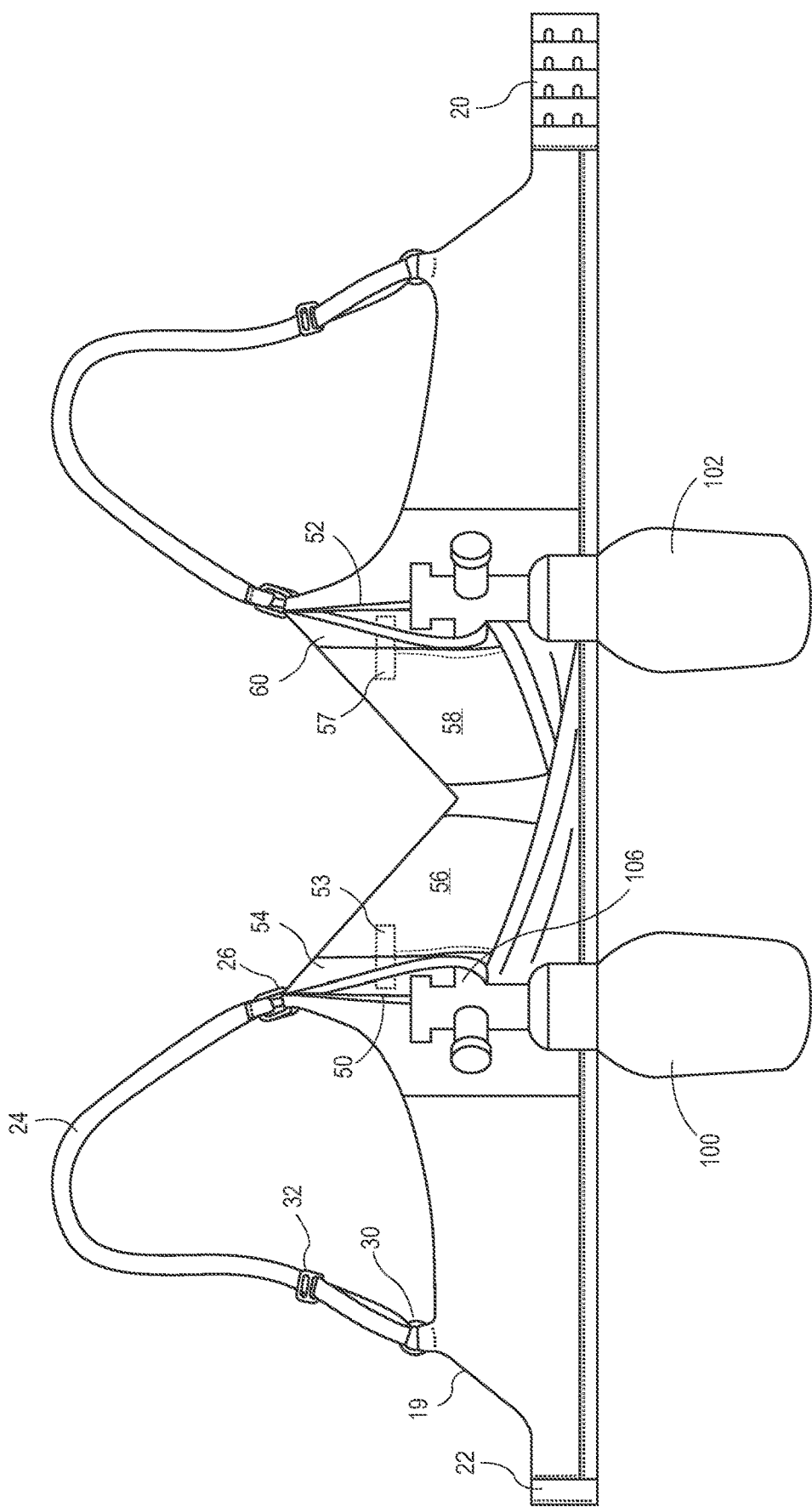
FIG. 14 is a front view of a garment according to an embodiment showing loops of the garment disposed around two breast pumping devices

FIGS. 10, 11, and 12 show the manner in which a breast shield may be inserted through an opening of the inner panel 19 of the garment 11. As illustrated in FIG. 11 and FIG. 14, for example, an elastic loop 52 may fit around the breast shield 104 and an elastic loop 50 may fit around breast shield 106 of a breast pump body. The elastic loop 52 may fit around any part of the breast shield 106, any piece that connects the breast shield to the bottle (e.g., milk container), and/or the bottle itself. In some embodiments, multiple loops may be used. For example, one loop may fit around the shield or any connector used and the second loop might secure the bottle itself. In some embodiments, the loop may be formed from an elastic material and in other embodiments, a more rigid material may be used that has less stretch/elasticity. For example, a less elastic material or fabric may be used with a slider to allow for adjustment of length. The loops may be removable and attached to the garment using a hook or other attachment mechanism.

Figure 13:
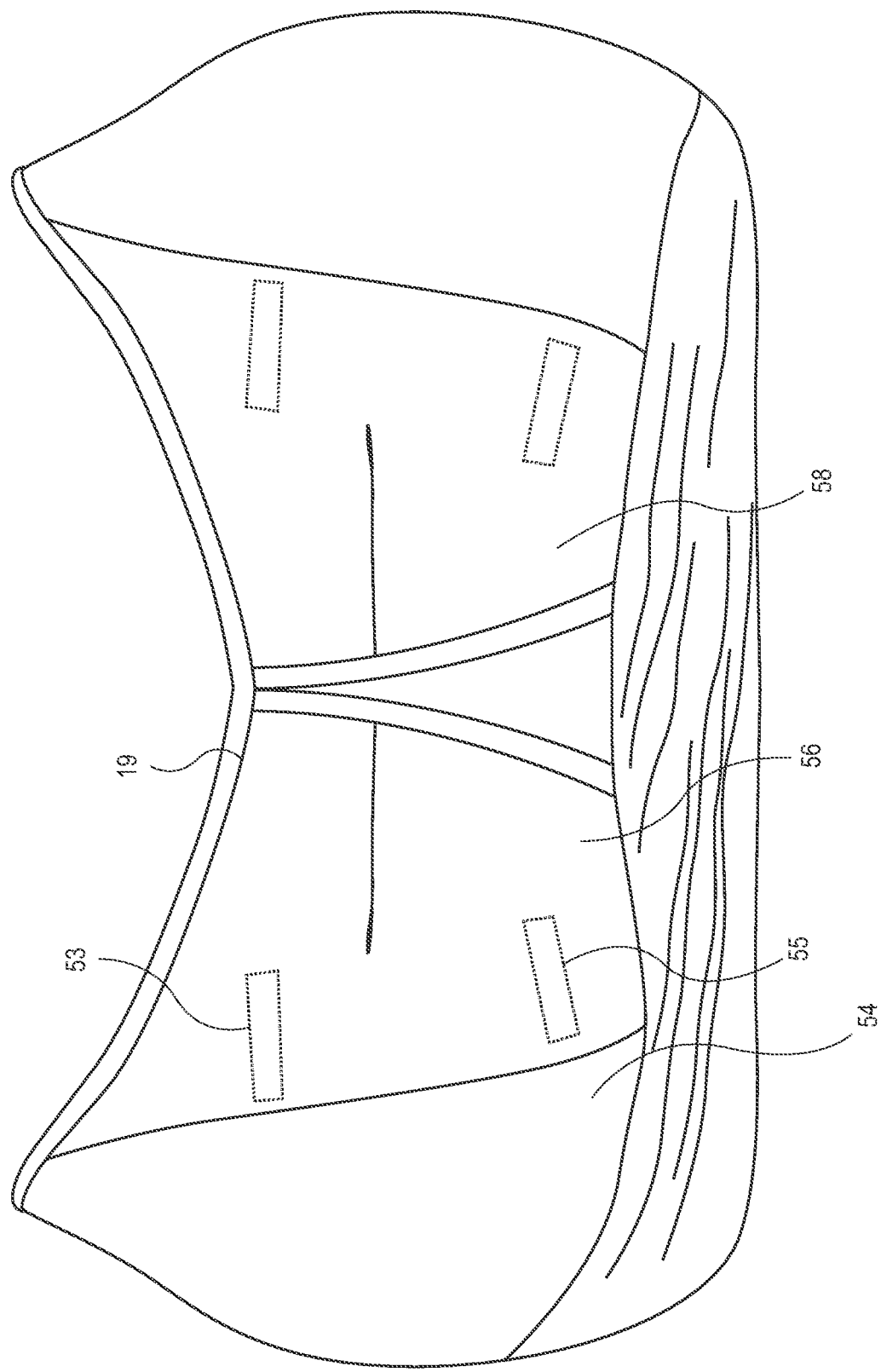
FIG. 13 is a front view of a garment according to an embodiment, illustrating the inner panel and stitching provided across a portion of the overlapping panels.

FIG. 13 illustrates the inner panel 19, as well as the rectangular shaped stitching 53, 55 provided across a portion of the overlapping panels 54, 56 to fasten the overlapping layers together and create an opening.

It is noted that based upon the comfort level of the woman during breast milk pumping, the woman may choose to utilize the elastic loops 50, 52 to hook/fit around the breast shield, without the utilization of any of the straps 46, 66, 72. Alternatively, the woman might utilize straps 46, 66, or 72 without employing the elastic loops 50, 52. Furthermore, the woman might utilize both the elastic loops 50, 52 along with one of the straps 46, 66, or 72.

Figure 15:
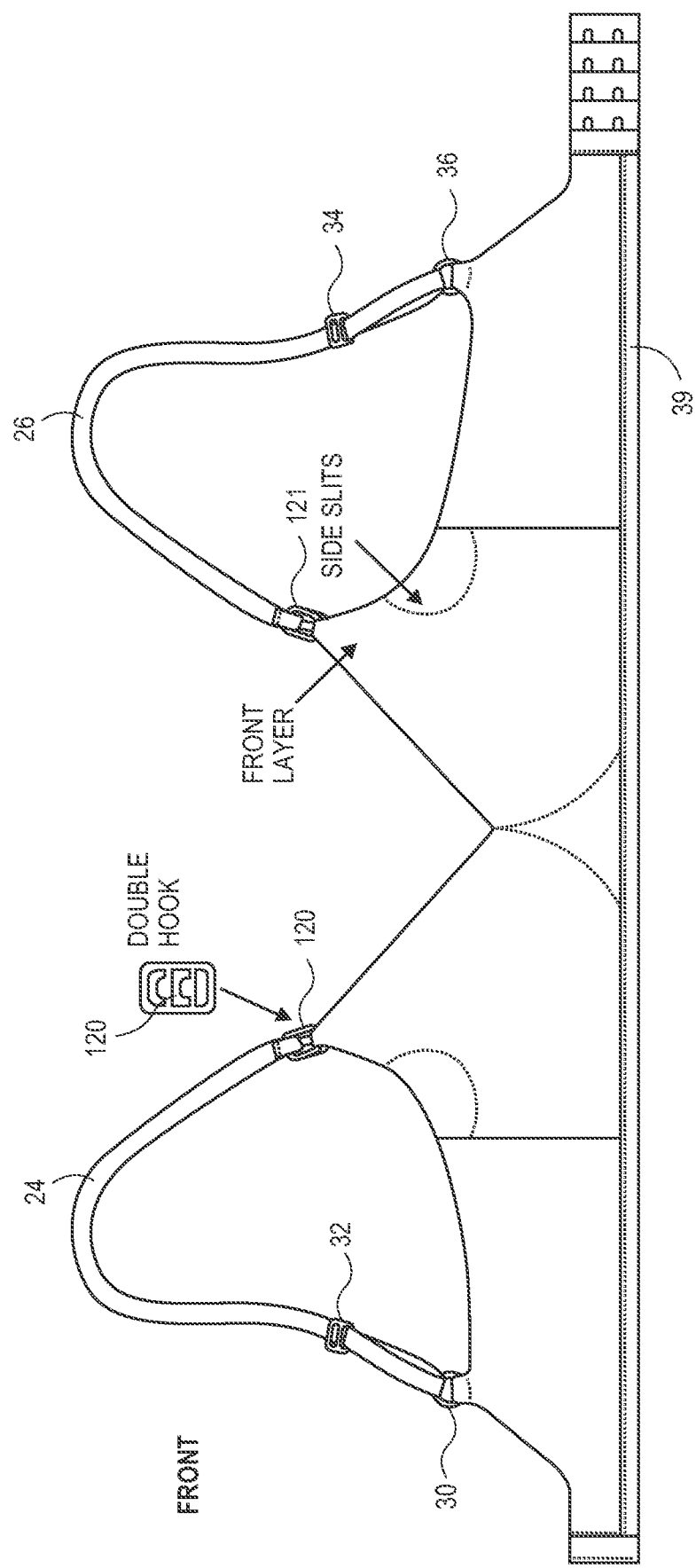
FIG. 15 is a front view of a garment according to an embodiment, illustrating use of a double hook attachment mechanism.
Figure 16:
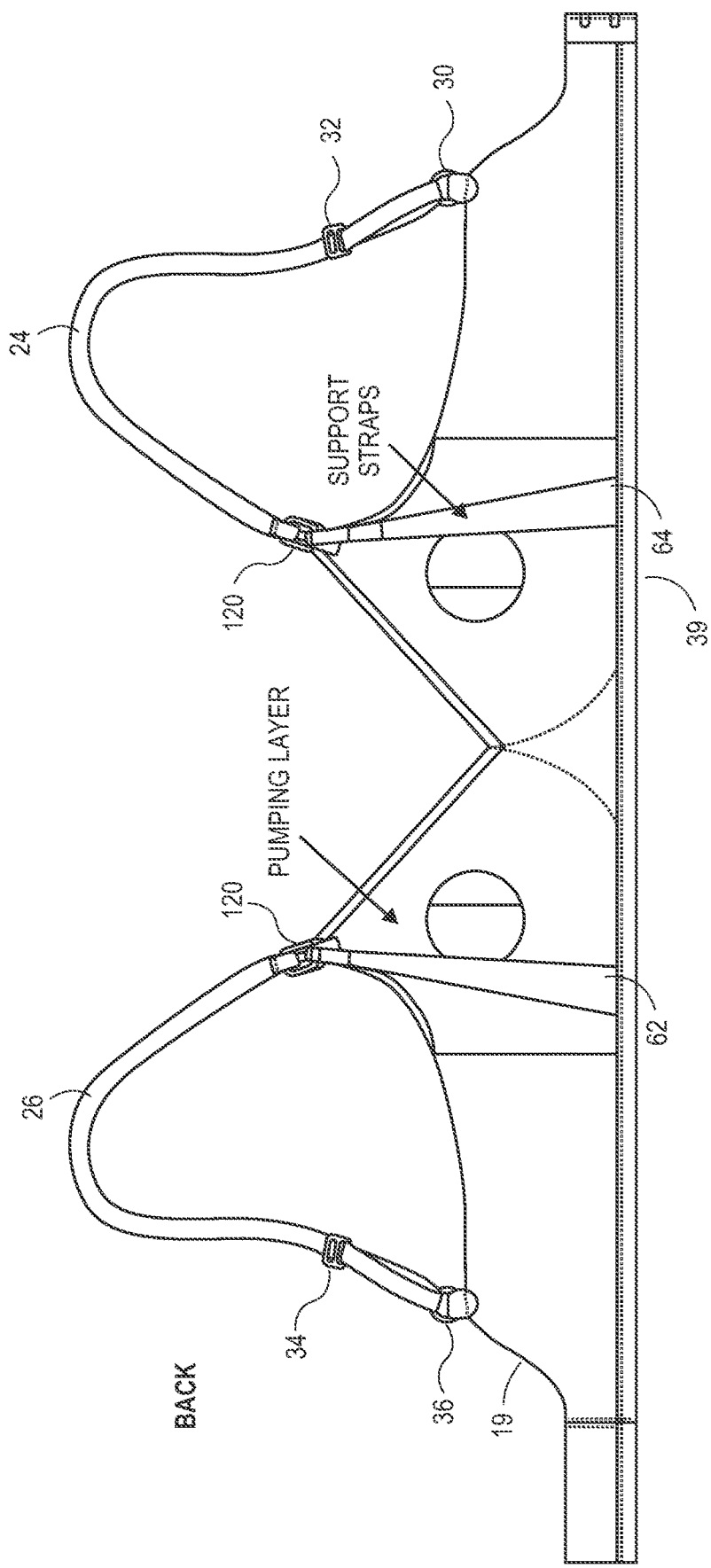
FIG. 16 is a rear view of the garment of FIG. 15, illustrating use of a double hook attachment mechanism.

FIGS. 15 and 16 depict an exemplary garment in accordance with some embodiments of the invention. FIGS. 15 and 16 illustrate use of a double hook attachment mechanism. The first end of the double hook is sewn on the shoulder strap and the second end of the double hook is sewn to the fabric stay 62 and/or 64. The outer or exterior surface 17 hooks to the top catch of the double hook 20 and the pump inner panel support hooks to the bottom catch of the double hook. The exterior surface 17 and inner panel 19 can be selectively hooked and unhooked from the catches of the double hooks.

The fabric stay 62 extends from the double hook 20 to the bottom 39 of the inner panel 19. Similarly, the fabric stay 64 extends from the double hook 20 to the bottom surface 39 of the pumping panel 19. The exterior surface 17 and inner panel 19 can be unhooked for nursing and reattached as desired. The fabric stays 62, 64 keep the shoulder straps secure on the shoulder, when the panels 16 and 18 are moved to allow for breast feeding. The inner panel 19 is provided with top rectangular shaped stitching 53 and a bottom rectangular shaped stitching 55 extending across a portion of the overlapping sections 54, 56 of the inner panel 19 to create an opening and provide support for a breast pump body. Similarly, a top rectangular stitching 57 and a bottom rectangular stitching 59 extend across a portion of the overlapping sections 58, 60 of the inner panel 19 to create an opening in and provide support for a breast pump body. FIGS. 15 and 16 illustrate side slits on each side of inner panel 19. The side slits may be wide enough to fit one or more fingers to allow for massage of the area.

Figure 17:
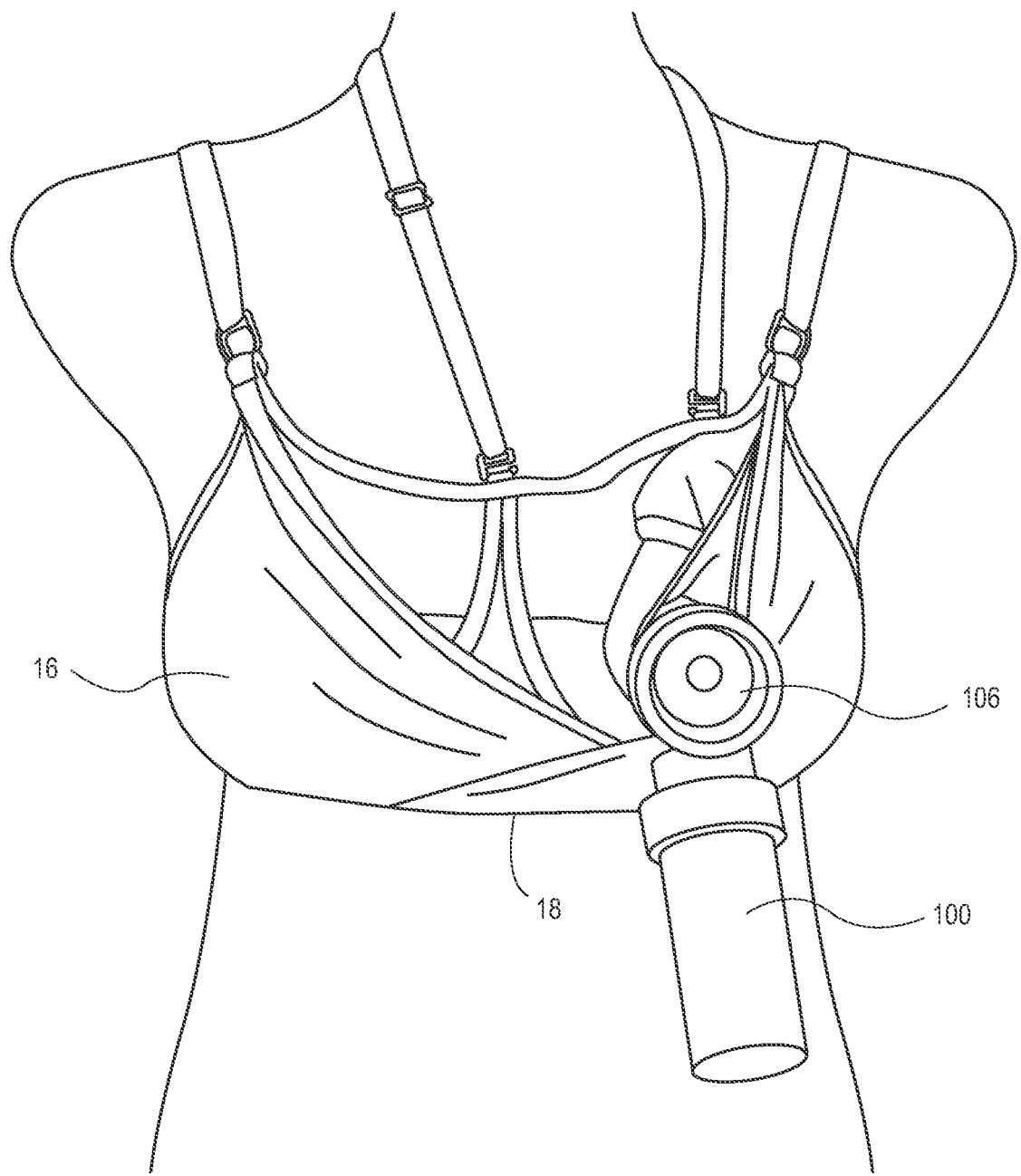
FIG. 17 is a front view of a garment according to an embodiment shown being worn by a wearer, and illustrating a strap attached to two corresponding attachment mechanisms on the garment for selective positioning of the strap.

FIG. 17 depicts an exemplary garment in accordance with some embodiments of the invention. FIG. 17 illustrates a strap attached to two corresponding attachment mechanisms on the garment 11 that are provided for selective positioning of the strap. As shown, the strap is positioned to provide support for the breast pump body 106 within an opening on a right facing side of the garment 11. The attachment mechanisms on the strap may be attached to various corresponding attachment mechanisms on the garment to support the breast pump body 106 as desired by the wearer. The positioning of the strap as shown is to provide support from the center and the left side (right facing side) of the garment 11 for the wearer.

Figure 18:
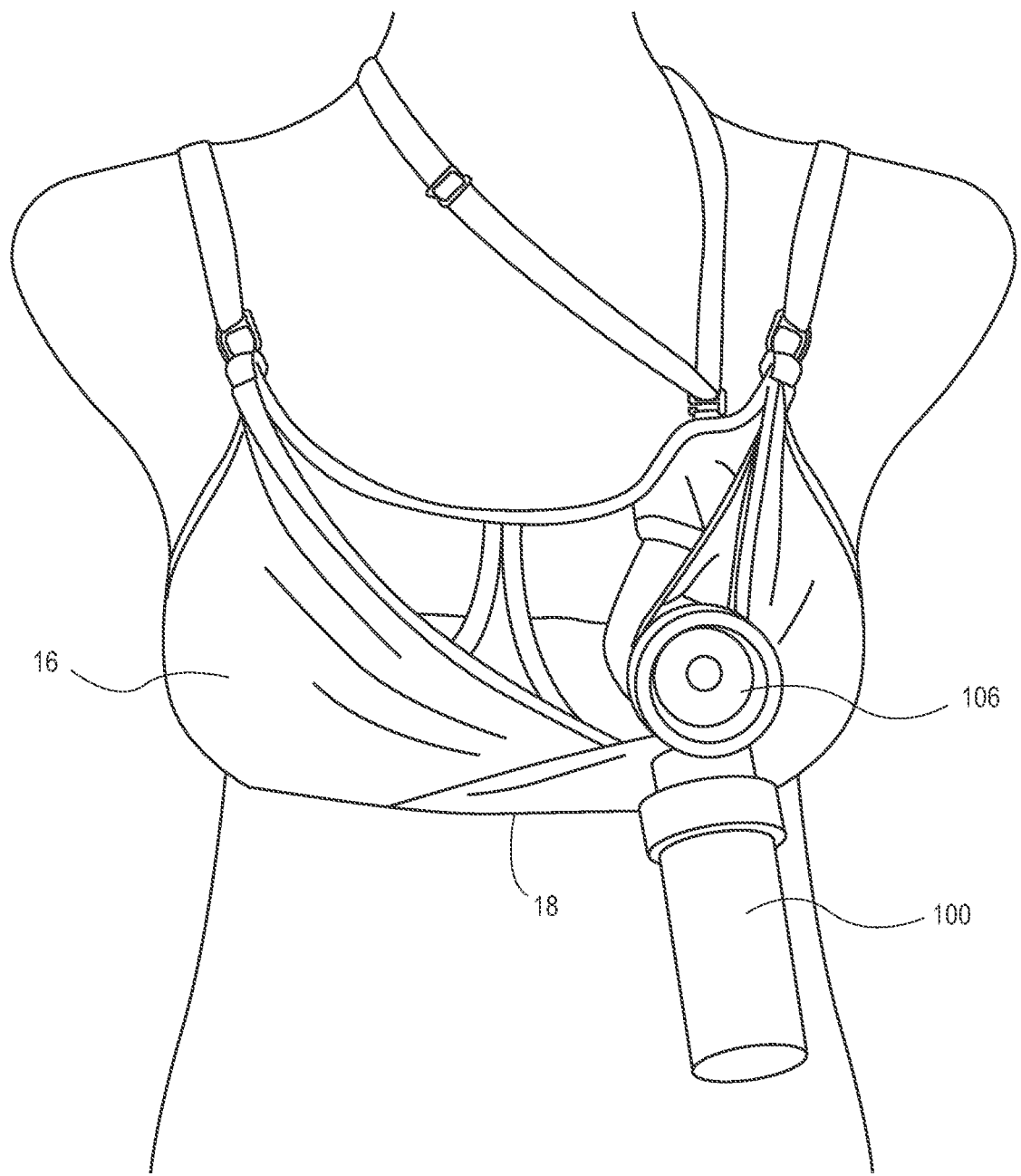
FIG. 18 is a front view of a garment according to an embodiment shown being worn by a wearer, and illustrating a strap attached to one attachment mechanism on the garment.

FIG. 18 depicts an exemplary garment in accordance with some embodiments of the invention. FIG. 18 shows a strap attached to one attachment mechanism on the garment 11. The strap is positioned to provide further support for a breast pump body 106 within the opening on the right facing side of the garment 11. The positioning of the strap is to provide support from the left side (right facing side) of the garment 11 for the wearer.

Figure 19:
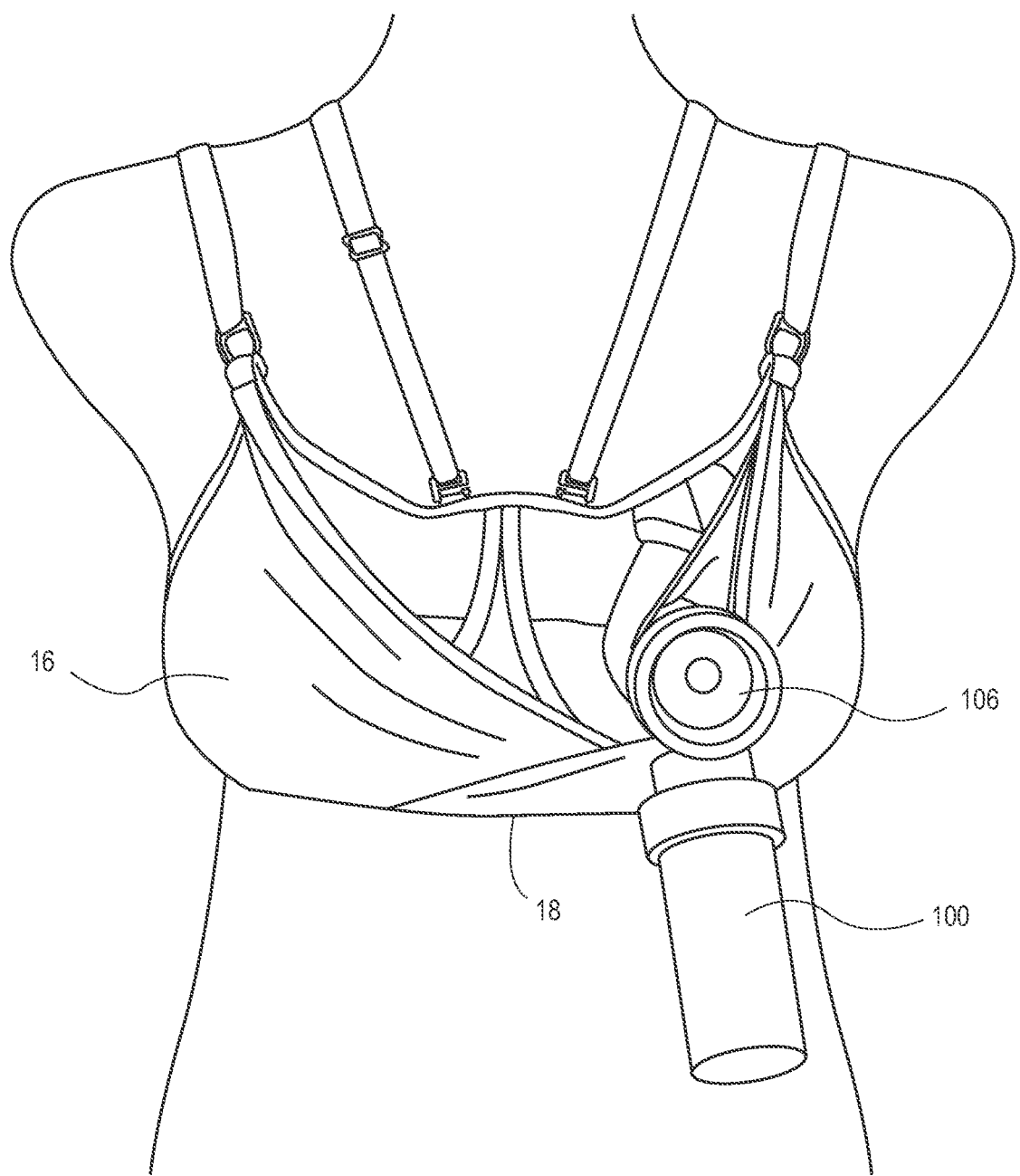
FIG. 19 is a front view of a garment according to an embodiment shown being worn by a wearer, and illustrating a strap positioned using attachment mechanisms to provide more support from the center.

FIG. 19 depicts an exemplary garment 11 in accordance with some embodiments of the invention. The strap is positioned using attachment mechanisms to provide more support from the center.

Figure 20:
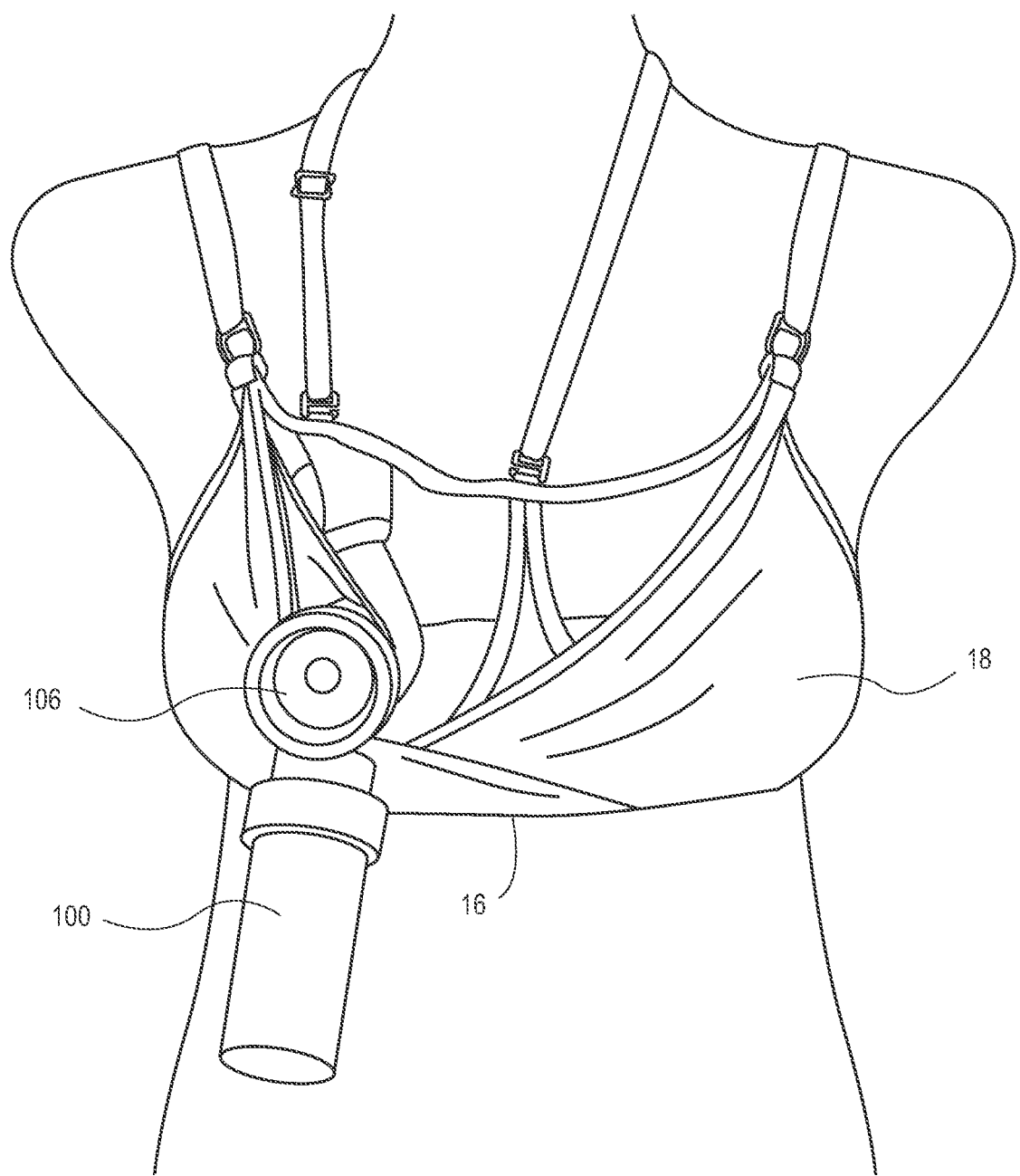
FIG. 20 is a front view of a garment according to an embodiment shown being worn by a wearer, and illustrating a strap positioned to provide support from the center and the right side of the garment.

FIG. 20 depicts an exemplary garment 11 in accordance with some embodiments of the invention. The strap is positioned to provide support from the center and the right side of the garment 11.

Figure 21:
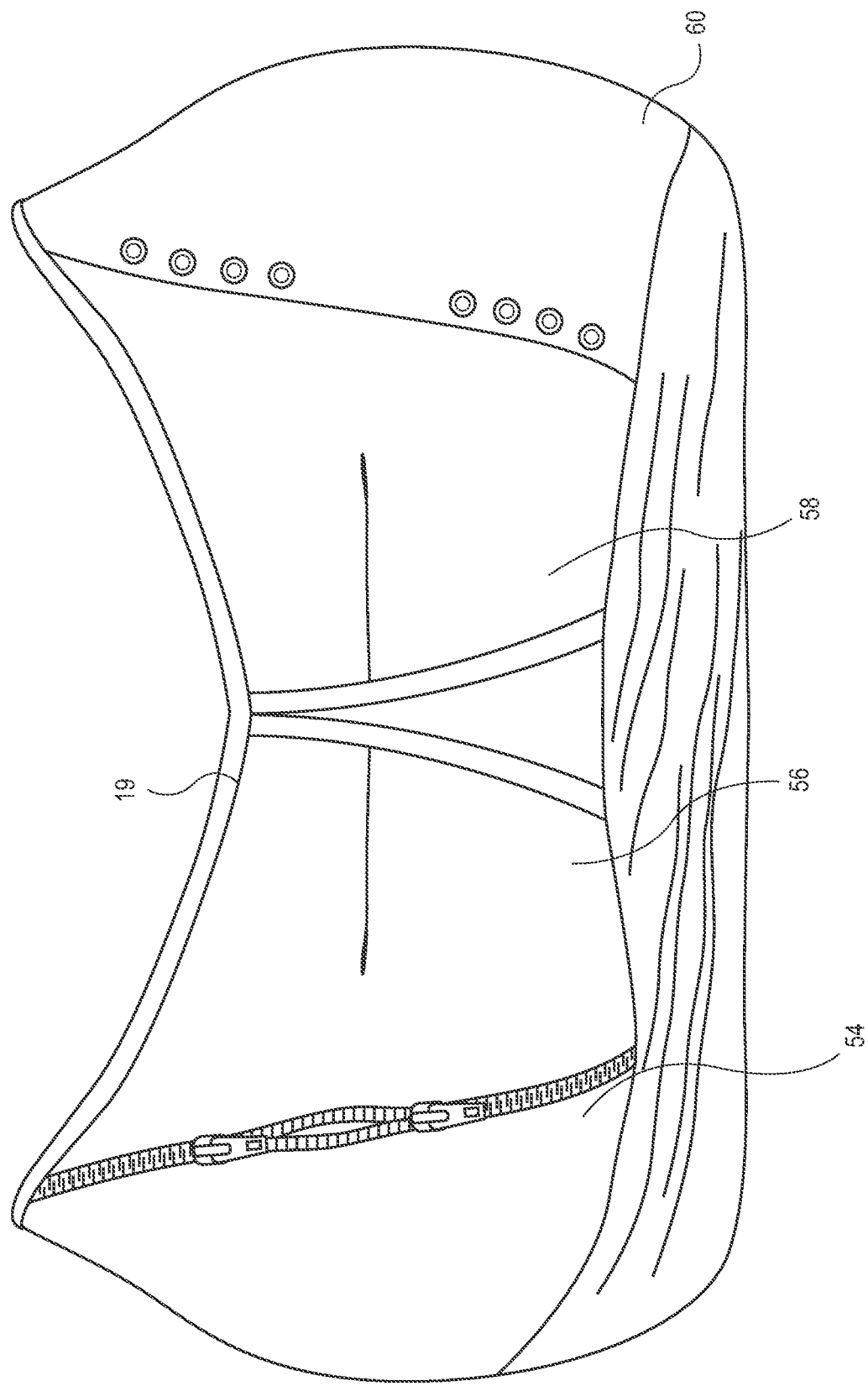
FIG. 21 is a front view of a portion of a garment according to an embodiment, illustrating a zipper used to fasten panels and form an opening for at least a portion of a breast pump.
Figure 22:
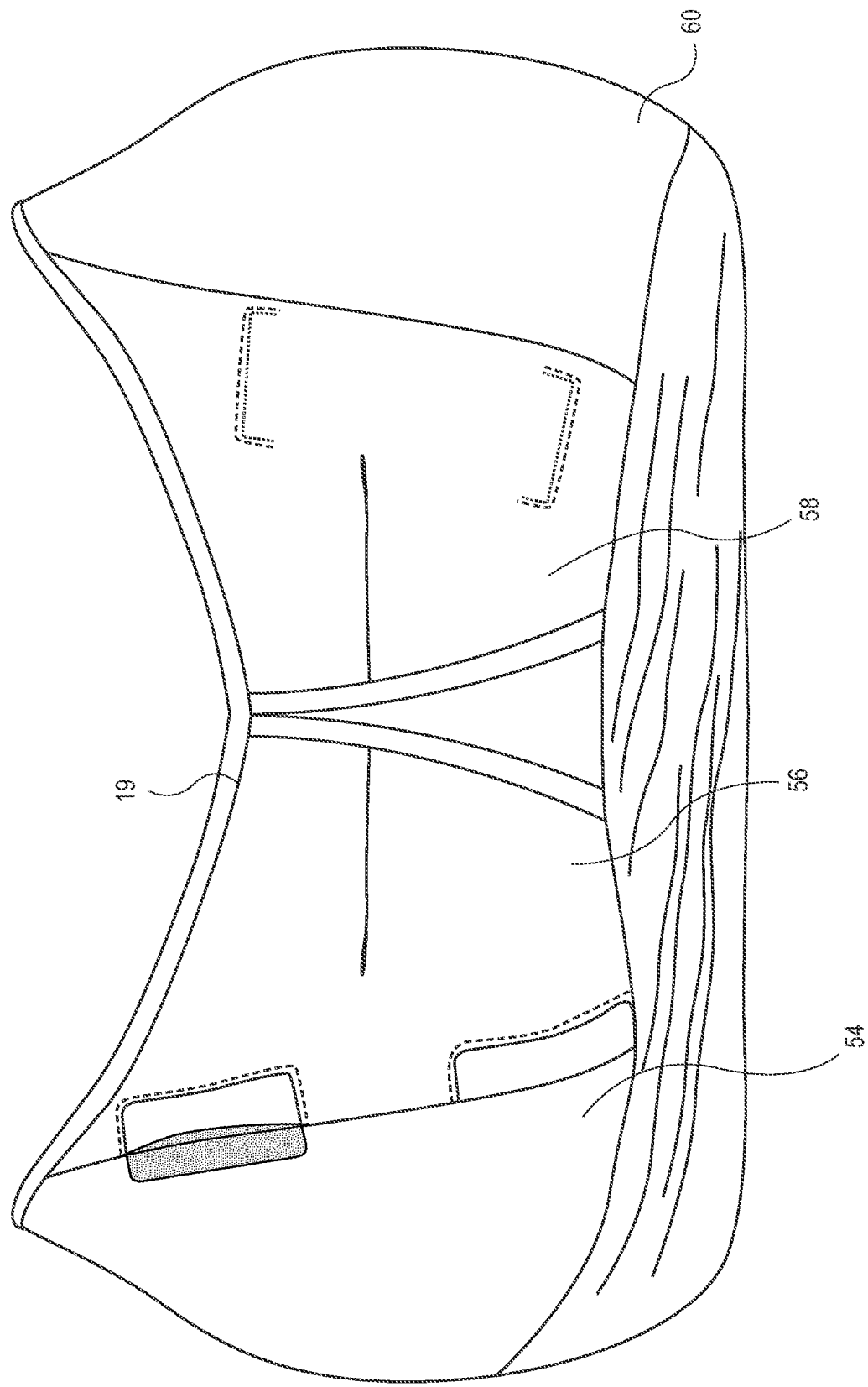
FIG. 22 is a front view of a portion of a garment according to an embodiment, illustrating hook and loop type fasteners used to fasten panels together.
Figure 23:
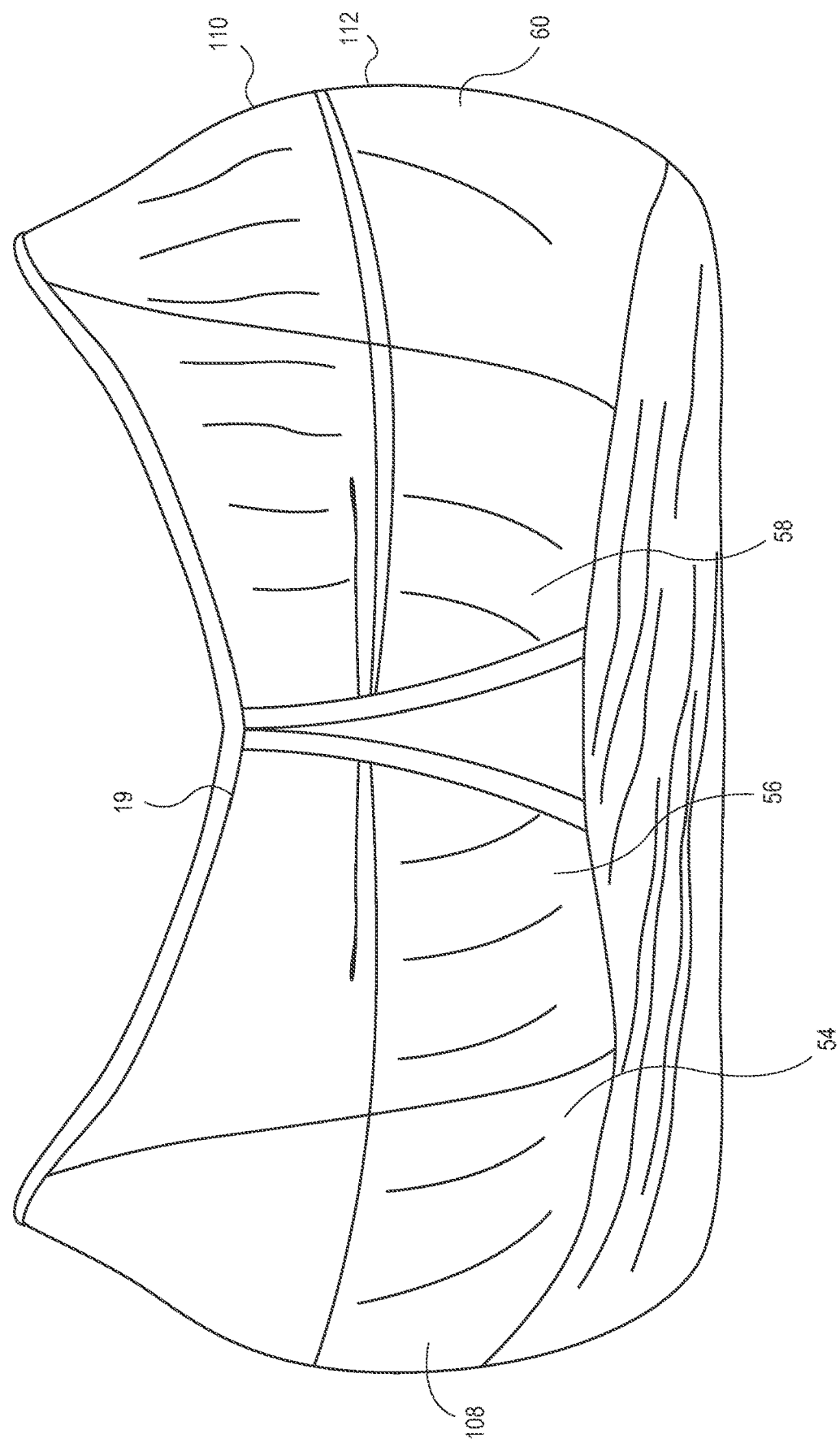
FIG. 23 is a front view of a portion of a garment according to an embodiment, illustrating layers of material provided under or over panels of the inner panel to provide additional support.

FIGS. 21-23 illustrate various embodiments of a garment. For description purposes, each garment may be depicted with different fastening mechanisms and/or panels of material to describe features that may be incorporated into the garment. Those with skill in the art will recognize one or more features described may be incorporated into the garment. For example, zippers and/or snaps may be used to fasten panels of the garment 11, as described in FIG. 21, and both types of fasteners are not required.

FIG. 21 depicts an exemplary garment 11 in accordance with some embodiments of the invention. As shown in FIG. 21, a zipper is used to fasten panels (e.g., 54 and 56) and form an opening for at least a portion of the breast pump. Alternatively and/or in addition to use of other fasteners, snaps may be used to fasten panels (e.g., 58 and 60) together to form an opening for at least a portion of the breast pump. The snaps may be snapped or unsnapped to adjust the size of the opening between panels. Stitching between the panels may or may not be used with other fasteners to fasten panels together. The fasteners may aid in further securing the panels together and keep the breast shield in place.

FIG. 22 depicts an exemplary garment 11 in accordance with some embodiments of the invention. As shown in FIG. 22, VELCRO® fasteners (e.g., hook and loop type fasteners) may be used to fasten panels together (e.g., panels 54 and 56). Stitched fasteners between panels (e.g., panels 58 and 60) may have elastic pieces stitched in to one or more of the edges of the stitching. The elastic pieces may provide additional support for keeping portions of the breast pump in place. The stitching may not have a rectangular shape as shown. One or more portions of the panels 58 and 60 may be stitched to fasten the panels together and create an opening.

FIG. 23 depicts an exemplary garment in accordance with some embodiments of the invention. Layers of material (e.g., 108, 110, and 112) may be provided under or over panels (e.g., 54, 56, 58, and 60) of the inner panel to provide additional support. For example, a layer of material 108 may be placed over at least a portion of panels 54 and 56 as shown and provide support for at least a portion of the breast pump. In other embodiments, the material 108 may be placed behind panels 54 and 56.

Figure 24:
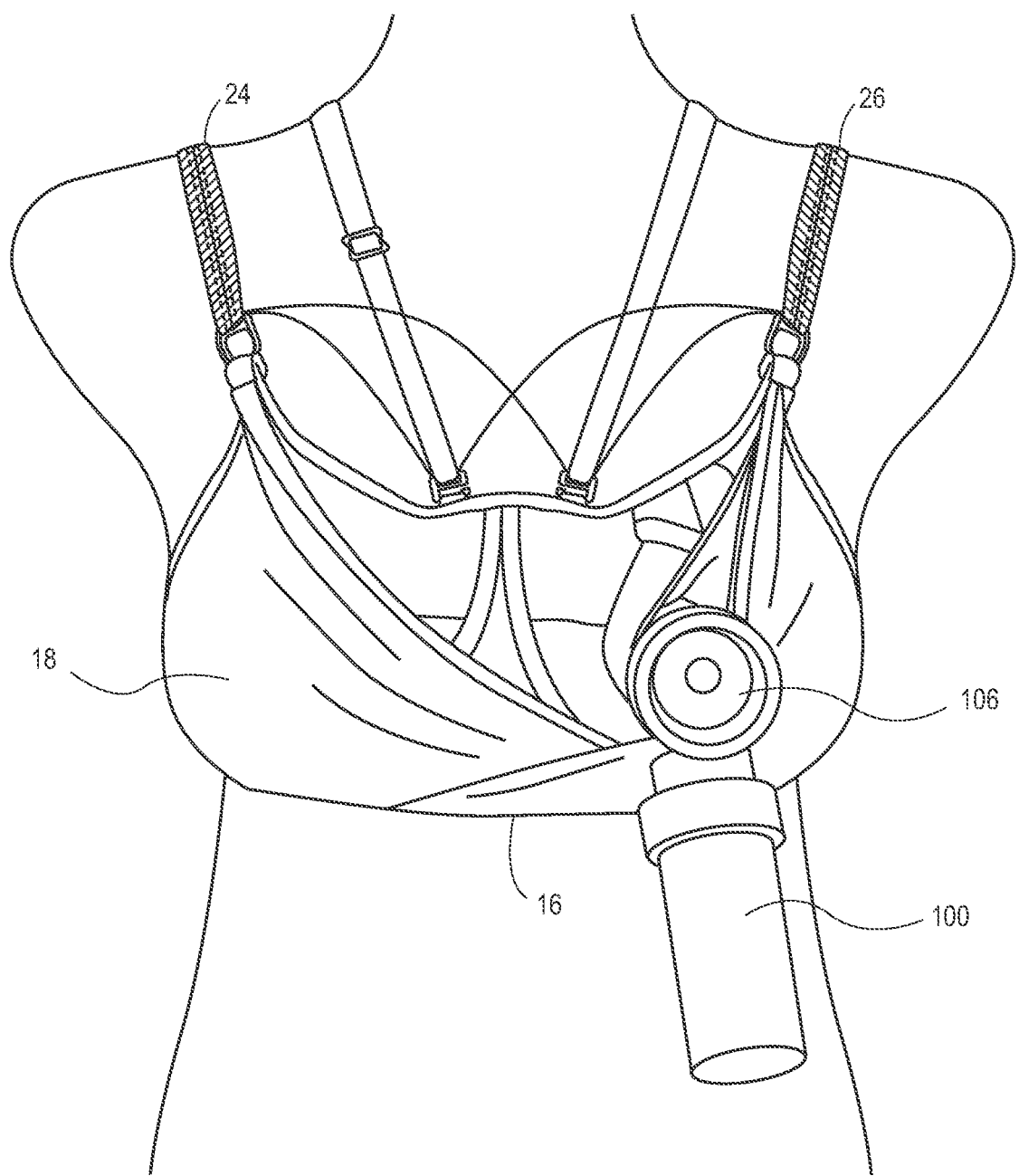
FIG. 24 is a front view of a garment according to an embodiment shown being worn by a wearer, and illustrating use of a channel or pocket within the straps of the garment.

FIG. 24 depicts an exemplary garment 11 in accordance with some embodiments of the invention. FIG. 24 illustrates use of a channel or pocket within the straps (e.g., 24 and 26) of the garment. The channel or pocket of the straps may house one or more cords, such as an elastic cord covered in a fabric that can be extracted and/or expanded and then attached to another portion of the garment as shown. The cord may be retracted and/or recoiled when not in use. The cord may have attachment mechanisms to allow for attachment to other portions of the garment. The cord may have sliders to allow for adjustment of the length.

Figure 25:
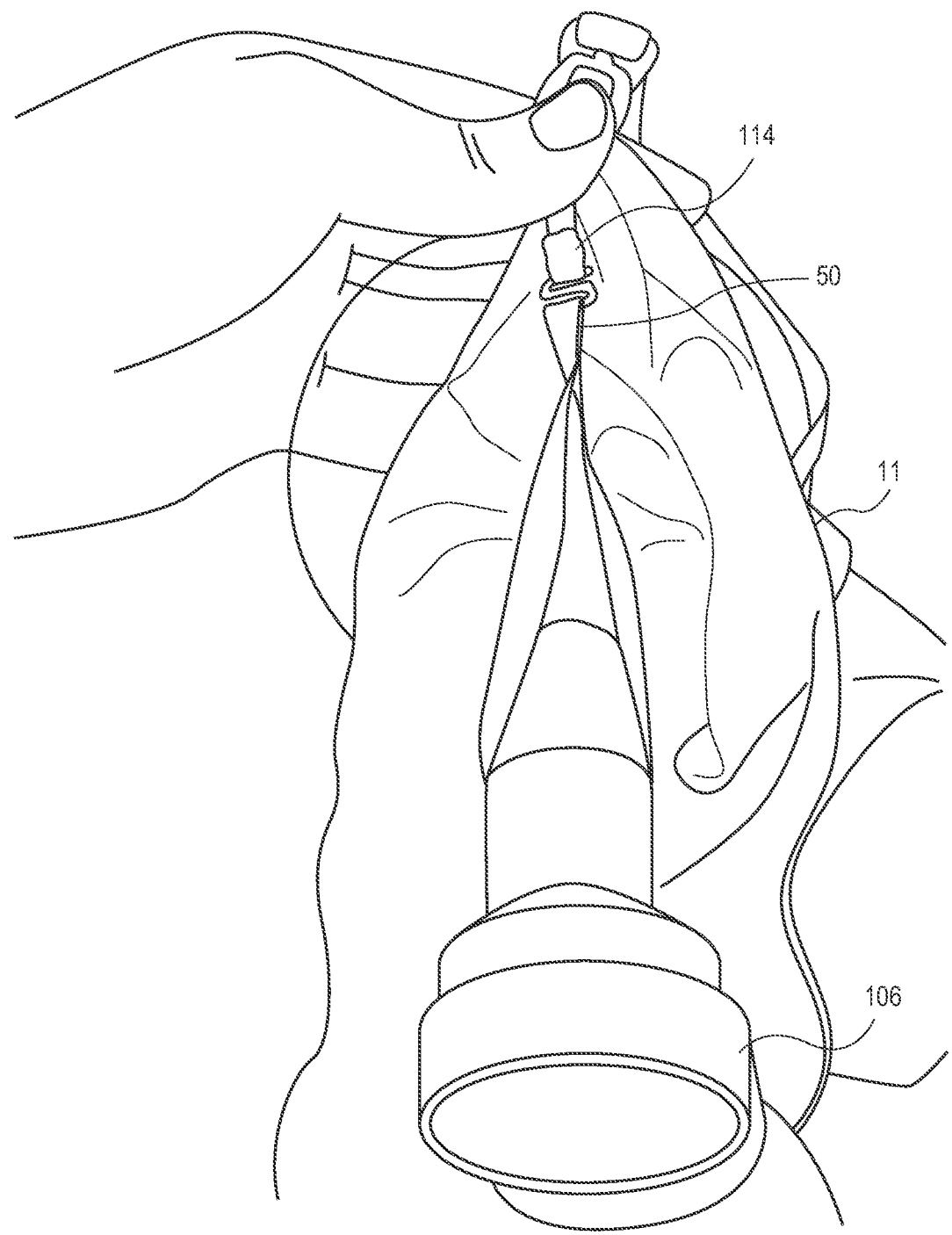
FIG. 25 illustrates a portion of a garment according to an embodiment having a detachable elastic loop.
Figure 26:
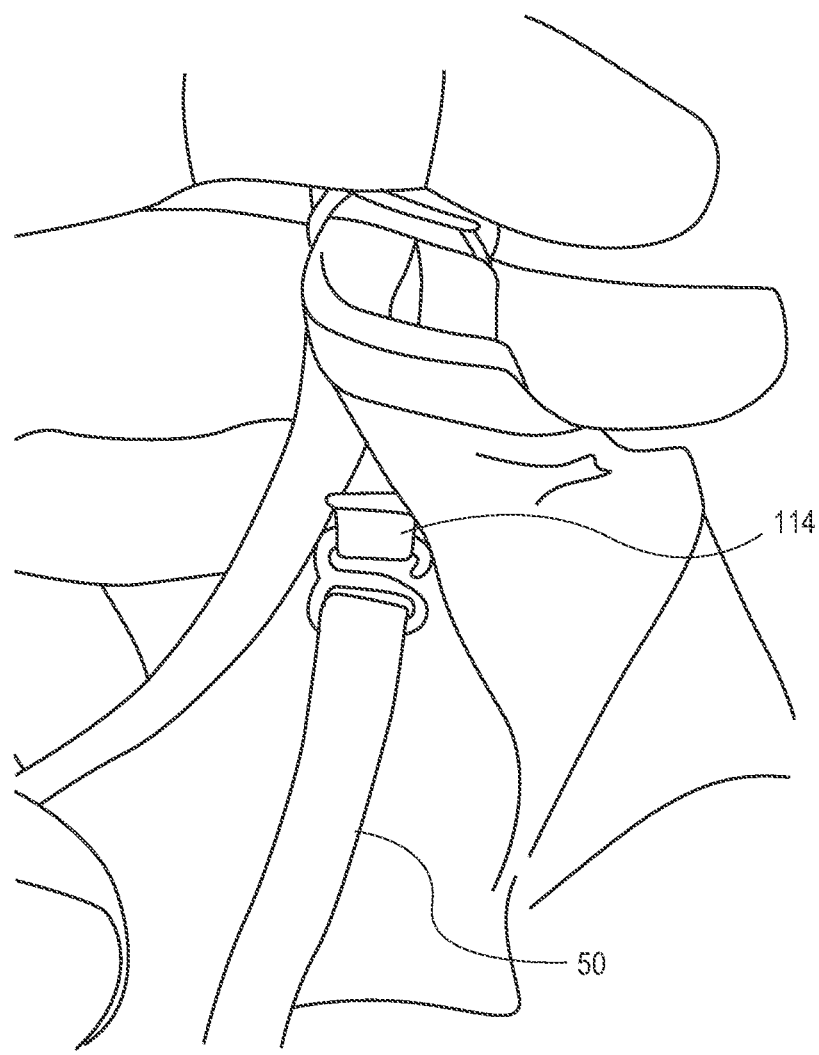
FIG. 26 illustrates a portion of a garment according to an embodiment having a detachable elastic loop.
Figure 27:
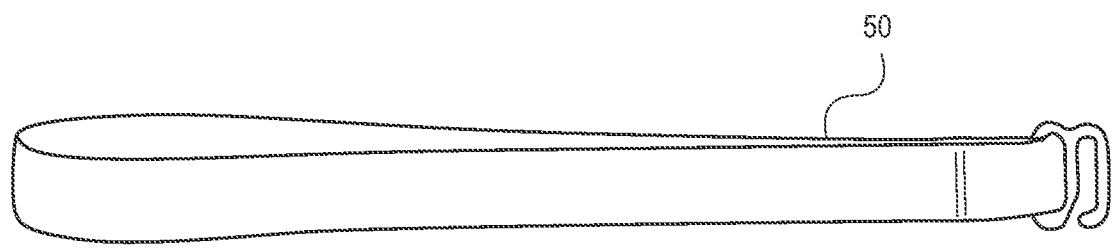
FIG. 27 is a side view of the detachable elastic loop of FIGS. 25 and 26.

FIGS. 25, 26, and 27 depicts an exemplary garment 11 in accordance with some embodiments of the invention with a detachable elastic loop 50. As shown, elastic loop 50 (and loop 52) may be selectively attached and/or detached from attachment mechanism 114 (e.g., a hook) on the garment.

Figure 28A:
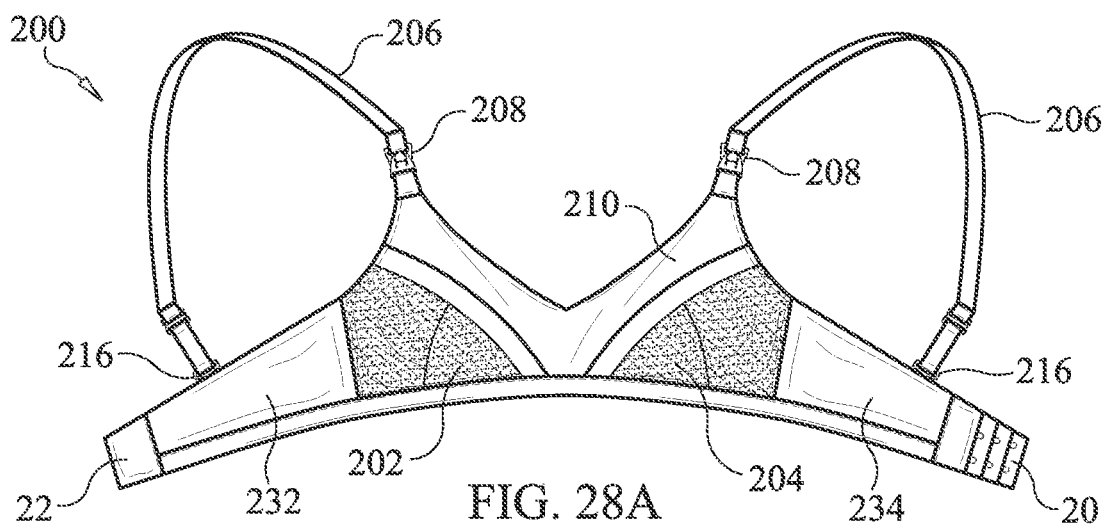
FIG. 28A is a front view of a garment according to another embodiment.

FIGS. 28A-28E illustrate various different views of a garment 200 in the form of a bra, to be worn around a chest or upper torso of a wearer, typically a woman, who may desire to express milk from one or both breasts using a breast pump. FIG. 28A illustrates a front view of an assembled garment 200, which can include an inner panel or pumping panel, an exterior panel, and a back panel. The inner panel, exterior panel and back panel can each include one or more separate panel material portions to, for example, form a right side panel and a left side panel of the garment 200. For example, the exterior panel can include a left side panel and a right side panel. In addition, one or more layers of material can be used to form each of the inner panel (pumping panel), exterior panel and/or back panel. For example, the inner panel can include 2, 3, 4 or more layers of material coupled together.

The exterior panel can include a first panel 202 and a second panel 204 (e.g., a right side panel and a left side panel, respectively). The pumping panel can include multiple layers of material that are coupled together in such a manner to define an opening or hole as described in more detail below. The layers of material can be coupled together such that at least a portion of the layers of material overlap each other. In some alternative embodiments, the layers of material may not overlap, but instead can be coupled together in an abutting or edge-to edge relationship to each other. In one embodiment, the layers of material include a center layer 210 (see, e.g., FIG. 28A), a left inner layer 214 (see, e.g., FIG. 28B) and a right inner layer 212 (see, e.g., FIG. 28B). The garment 200 can include first and second shoulder straps 206 (also referred to as "shoulder straps") having a fastening mechanism 216 coupled to a first end, and a second end of each of first and second shoulder straps 206 being attachable to first and second engagement mechanisms 208. The garment 200 also includes closures 20 and 22, a first wrap-around panel 232, and a second wrap-around panel 234. For ease of discussion, center layer of material 210 may also be referred to herein as "center layer 210." The closures 20 and 22 can be constructed the same as or similar to, and function the same as or similar to the double hook attachment mechanisms 20, 22 described above.

The components of garment 200 (e.g., panels and/or layers) may be made from any appropriate material, including, but not limited to, fabric, cotton, spandex, elastic, polyester, rayon, and mesh. Where appropriate, one or more of the components may be fabricated to stretch or be temporarily reshaped and/or repositioned. In one embodiment, first panel 202 and second panel 204 may be made from a lightweight material that may, in some instances, include a decorative design or accent (e.g., lace or decorative pattern). First panel 202 and/or second panel 204 may serve to, for example, smooth the exterior surface of garment 200 so as to provide a seamless appearance when worn under another garment (e.g., shirt or blouse). In some embodiments, first panel 202 and/or second panel 204 may assist in the positioning, support, and/or retention of a portion of a breast pump, such as breast shield(s) 104 of the breast pump described above, within an opening 230, as discussed below with regard to FIG. 28B. Additionally, or alternatively, first panel 202 and/or second panel 204 may assist in the positioning, support, and/or retention of a portion of a pumping container, such as pumping container 100 (described above) within opening 230 and/or a breast pad, such as breast pad 240, which will be discussed in greater detail below with regard to FIGS. 30A-30C.

First and second wrap around panels 232 and 234 may be affixed to a portion of, for example, the exterior panel or the pumping panel or the back panel, or any combination of these panels, and may serve to wrap around the body of a wearer (typically the side and back) so that the garment 200 may close around the wearer via closures 20 and 22 in a manner similar to known garments/brassieres.

Figure 28B:
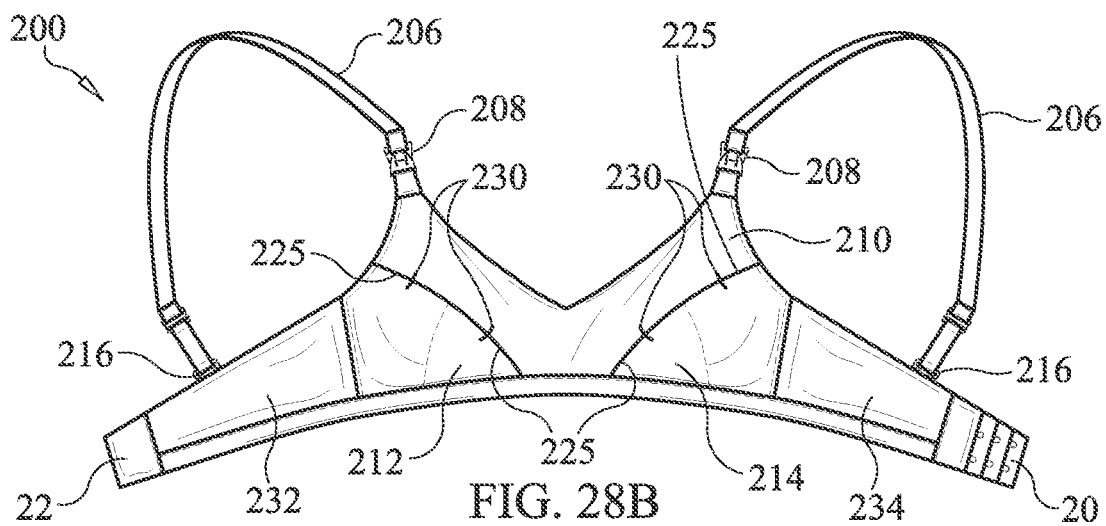
FIG. 28B is a front view of the garment of FIG. 28A with an outer layer removed to illustrate a front view of a middle layer of the garment.

FIG. 28B illustrates a front view of garment 200, without first panel 202 and second panel 204 of the exterior panel so as to expose a left inner layer 214 and a right inner layer 212. The left inner layer 214 may be situated on the left side of garment 200 (covering the left breast), within the pumping panel, and arranged so as to partially overlap a portion of center layer 210 positioned on the left side of the garment 200. Left inner layer 214 may be partially affixed (e.g., via sewing, chemical bonding, heat bonding, etc.) to center layer 210 at upper and/or lower affixed regions 225. A region, between the upper and lower affixed regions 225, where the left inner layer 214 and the center layer 210 are not affixed to one another defines an opening 230 between the left inner layer 214 and the center layer 210.

The right inner layer 212 may be situated on the right side of garment 200 (covering the right breast) and arranged so as to partially overlap a portion of center layer 210 positioned on the right side of the garment 200. Right inner layer 212 may be partially affixed (e.g., via sewing, chemical bonding, heat bonding, etc.) to center layer 210 at upper and/or lower affixed regions 225. A region between the upper and lower affixed regions 225 where the right inner layer 212 and the center layer 210 are not affixed to one another defines an opening 230 between the right inner layer 212 and the center layer 210.

In this embodiment, an attachment line (e.g., stitching) of the affixed regions 225 between the right inner layer 212 and the center layer 210 and between the left inner layer 214 and the center layer 210 (e.g., overlapping material portions) and/or opening(s) 230 are obliquely oriented at an angle relative to the bottom edge of the garment 200. Exemplary angles for the attachment line of the partially overlapping and/or overlapped left inner layer 214 and center layer 210 may include any angle within the range of about 30° to about 80° relative to the bottom edge of the garment 200 and exemplary angles for the attachment line of the partially overlapping and/or overlapped right inner layer 212 and center layer 210 may include any angle within the range of about 100° to about 150° (i.e., about −30° to about −80° relative to the bottom edge of the garment 200. Thus, each of the openings 230 is angled in a direction upwardly from a center of the garment. In some embodiments, the oblique orientation of the opening 230 may be substantially (+/− 10%) 45° or 135° for the opening 230 on the first and second side of garment 200, respectively. In some alternative embodiments, the angle of the attachment lines and openings 230 can be angled in an opposite direction. For example, the attachment line on the right side of the bra can angle downwardly from a top edge of the bra toward the wrap around panel 234 (e.g., at an angle in the range of about 30° to about 80° relative to the bottom edge of the garment 200) and the attachment line on the left side of the bra can angle downwardly from a top edge of the bra toward the wrap around panel 232 (e.g., at an angle in the range of about 100° to about 150° relative to the bottom edge of the garment 200).

Opening(s) 230 may be sized and positioned within the garment 200 so as to allow at least a portion of a breast pump, such as a breast shield 104 of the breast pump, to be inserted into the opening(s) 230 and contact the wearer's breast(s). In one embodiment, insertion of a breast shield 104 into opening 230 may be achieved by separating a portion of the center layer 210 positioned between affixed regions 225 from the left inner layer 214 and/or the right inner layer 212. The separation may be achieved by lifting, pushing and/or pulling the center layer 210, the left inner layer 214, and/or the right inner layer 212 into a desired configuration. The overlapping portions of right inner layer 212 and center layer 210 and left inner layer 214 and center layer 210 defining the openings 230 provide a width or depth of material that defines a passageway to support at least a portion of the breast pump (e.g., breast shield 104) inserted therethrough.

The oblique angle of the opening(s) 230 can provide flexibility and movement of the portion of the breast pump along the oblique angle of the opening 230 so as to, for example, align with a nipple of the wearer's breast or breasts. Thus, a user/wearer can have improved ability to position the breast pump at a desired angle and/or orientation within the opening 230. For example, the oblique angle of the opening 230 can allow the wearer to reposition the breast pump left-to-right and/or up/down within the opening 230. The oblique opening 230 can also provide increased support of the breast pump as the pumping container (e.g., milk bottle) increases in weight from collection of the expressed milk. In some embodiments, first panel 202 and/or second panel 204 may be moved or repositioned by a wearer so as to access opening(s) 230. In some cases, first panel 202 and/or second panel 204 may be removed, either from garment 200, or pulled down to expose center layer 210, left inner layer 214, right inner layer 212 and/or opening 230. In some embodiments, garment 200 may not include first panel 202 and/or second panel 204. In these embodiments, movement of the center layer 210, left inner layer 214, and/or right inner layer 212 may expose opening 230.

Figure 28C:
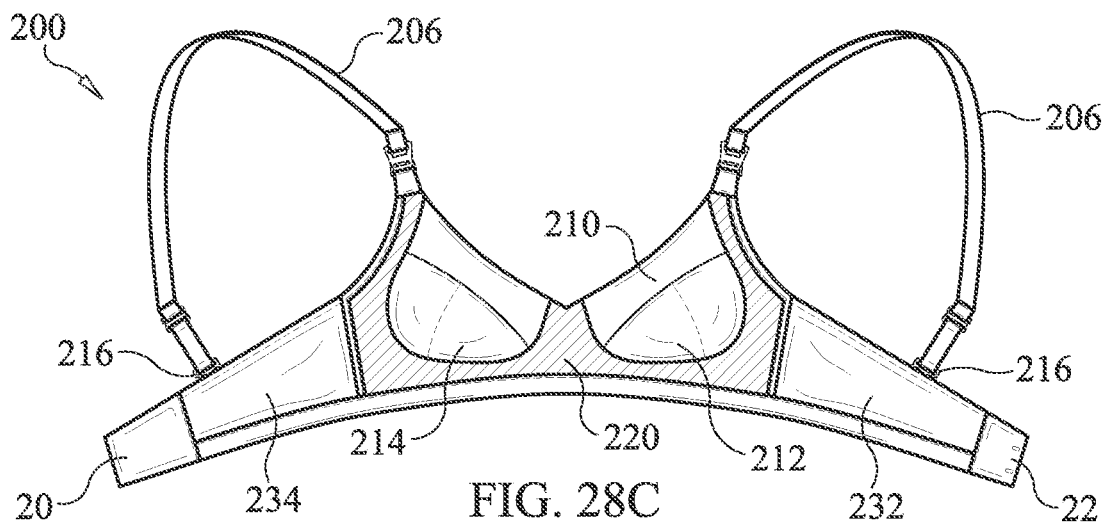
FIG. 28C is a rear view of the garment of FIG. 28A.

FIG. 28C illustrates a back or rear view of garment 200, which shows an optional back panel 220. Back panel 220 may serve to provide structural support for the garment 200 as well as the wearer's breasts when worn. In some embodiments, back panel 220 may be made of a material, or layers of material, that are more stiff than, for example, center layer 210, the left inner layer 214, the right inner layer 212, first panel 202, and/or second panel 204. Back panel 220 may be configured in a "w"-type of shape, wherein there is material for the back panel 220 in the center and sides and two curve-shaped cutout sections with no material. The curve-shaped cutout sections may be configured to align with and fit underneath/around the wearer's breasts. It will be understood by those of skill in the art that "material" as used herein is not limited to a single panel or layer of fabric and may be any combination materials or layers of material.

It should be noted that in some instances, garment 200 may not include optional back panel 220. In these instances, for example, a bottom edge of first wrap around panel 232, center layer 210, left inner layer 214, right inner layer 212, and/or second wrap around panel 234 may be affixed to one another and/or to a strap (not shown) or other mechanism for facilitating the construction of garment 200 and/or the attachment of closures 20 and 22. Additionally, when back panel 220 is not included in garment 200, first and second portions of engagement mechanisms 208 (described in detail below with reference to FIGS. 29A and 29B) may be attached to, for example, center layer 210, left inner layer 214, and/or right inner layer 212, respectively.

Additionally, center layer 210, left inner layer 214, right inner layer 212, and back panel 220 may include one or more different layers, pieces of fabric, panels, etc. affixed (e.g., sewn, chemically bonded, etc.) to one another.

Figure 28D:
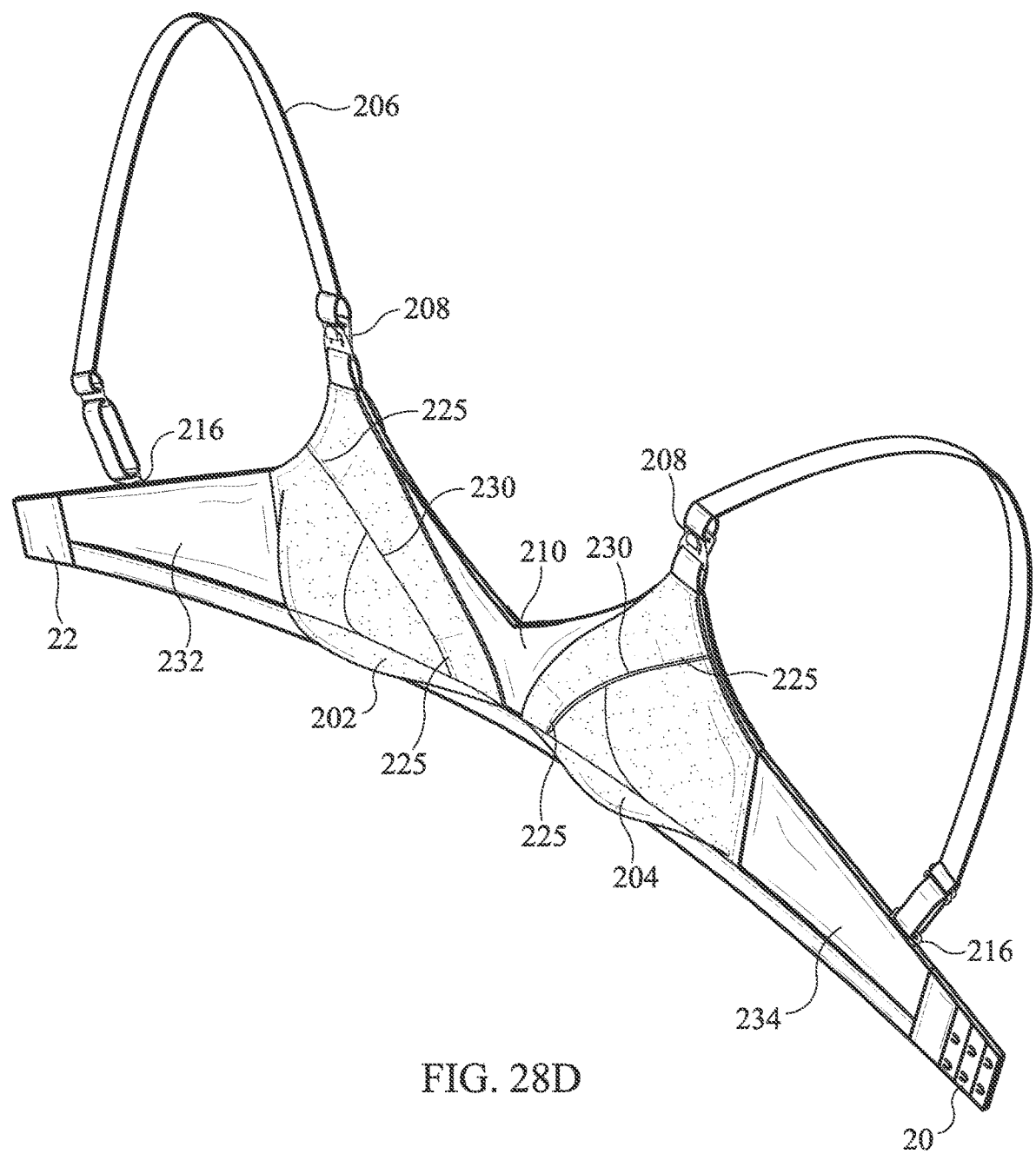
FIG. 28D is a front perspective view of the garment of FIG. 28A.
Figure 28E:
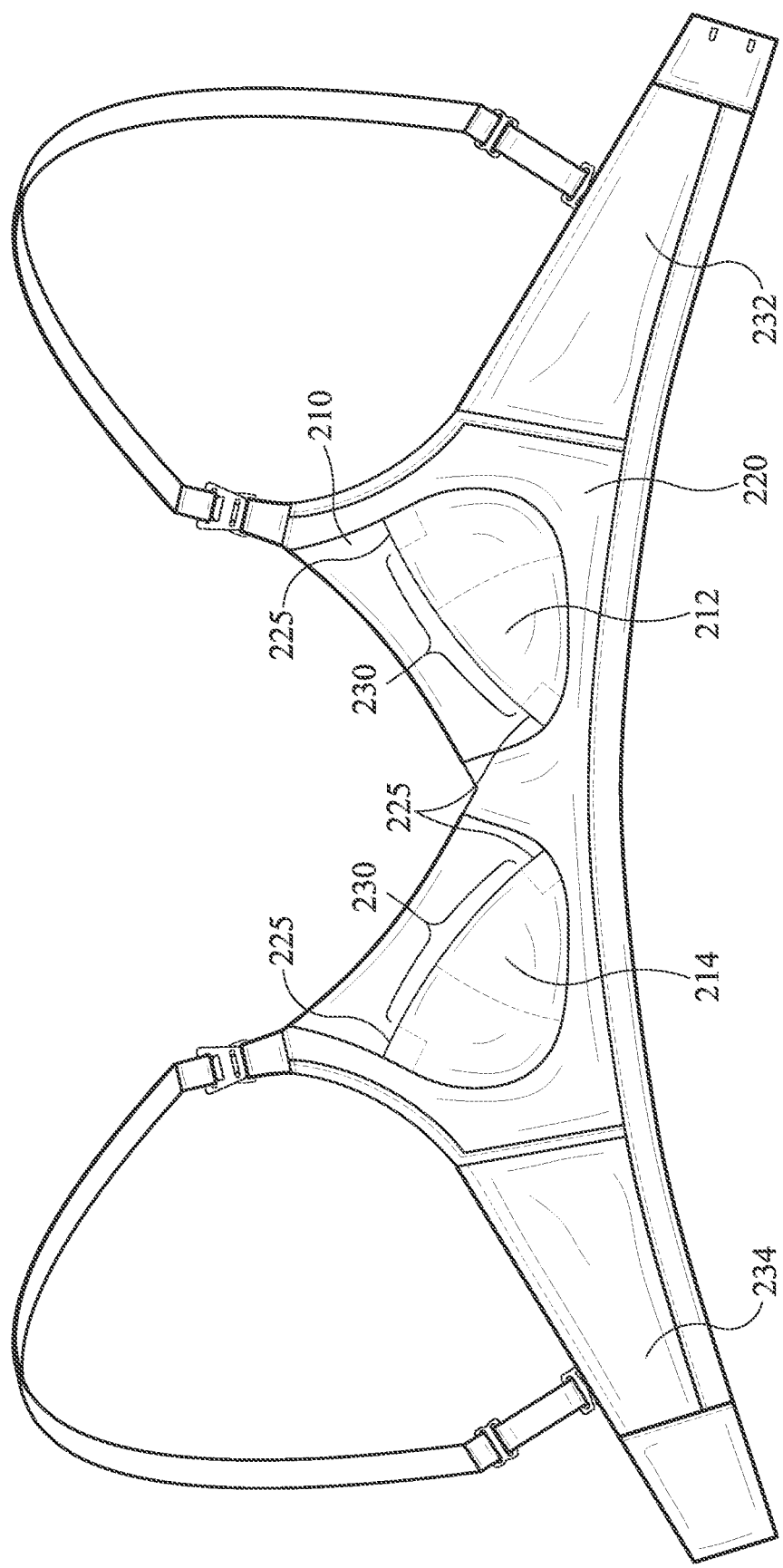
FIG. 28E is a rear view of the garment of FIG. 28A illustrating affixed regions and openings of the garment that can receive a portion of a breast pumping device therethrough.

FIG. 28D provides a perspective illustration of the garment 200 showing how first panel 202, second panel 204, center layer 210, left inner layer 214, and/or right inner layer 212 may extend perpendicularly or substantially perpendicularly, outward from a planar surface of garment 200 so as to, for example, accommodate a three dimensional shape of a wearer's breasts. Additionally, FIG. 28D also illustrates that upper and/or lower affixed regions 225 are sewn and a region therebetween allows for opening 230. FIG. 28E provides an alternative rear view of garment 200 showing affixed regions 225 and openings 230.

Figure 29A:
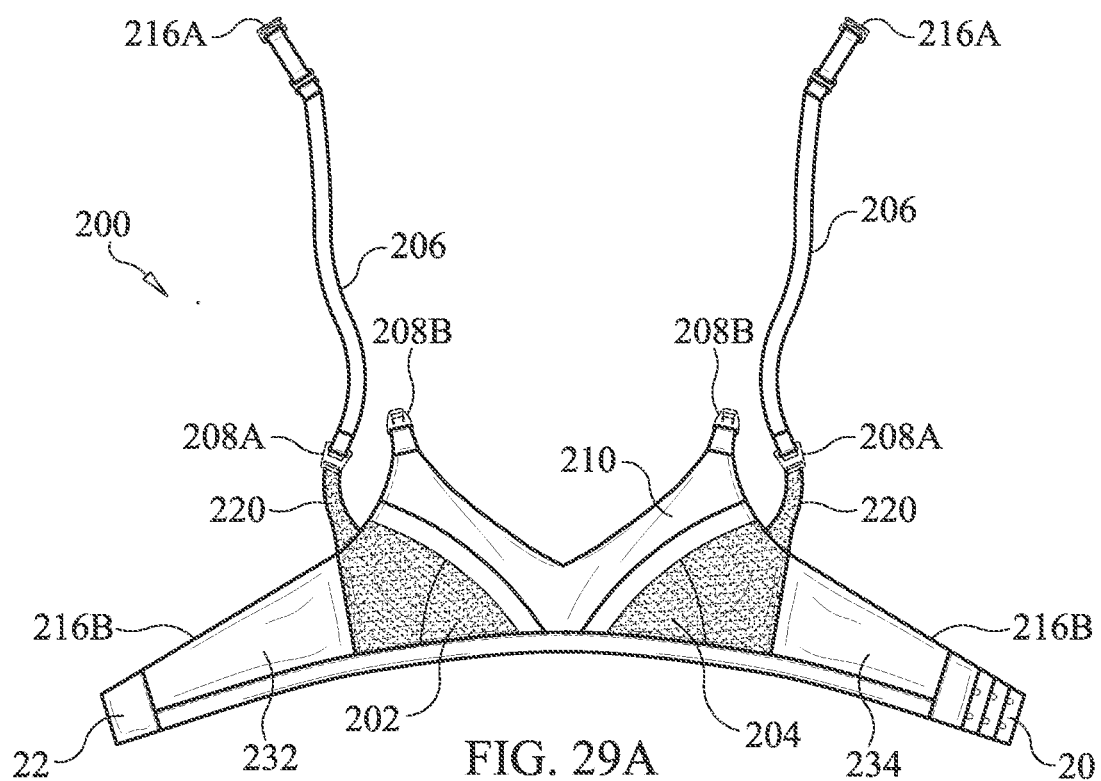
FIG. 29A is a front view of the garment of FIG. 28A showing an engagement mechanism in a disengaged position.
Figure 29B:
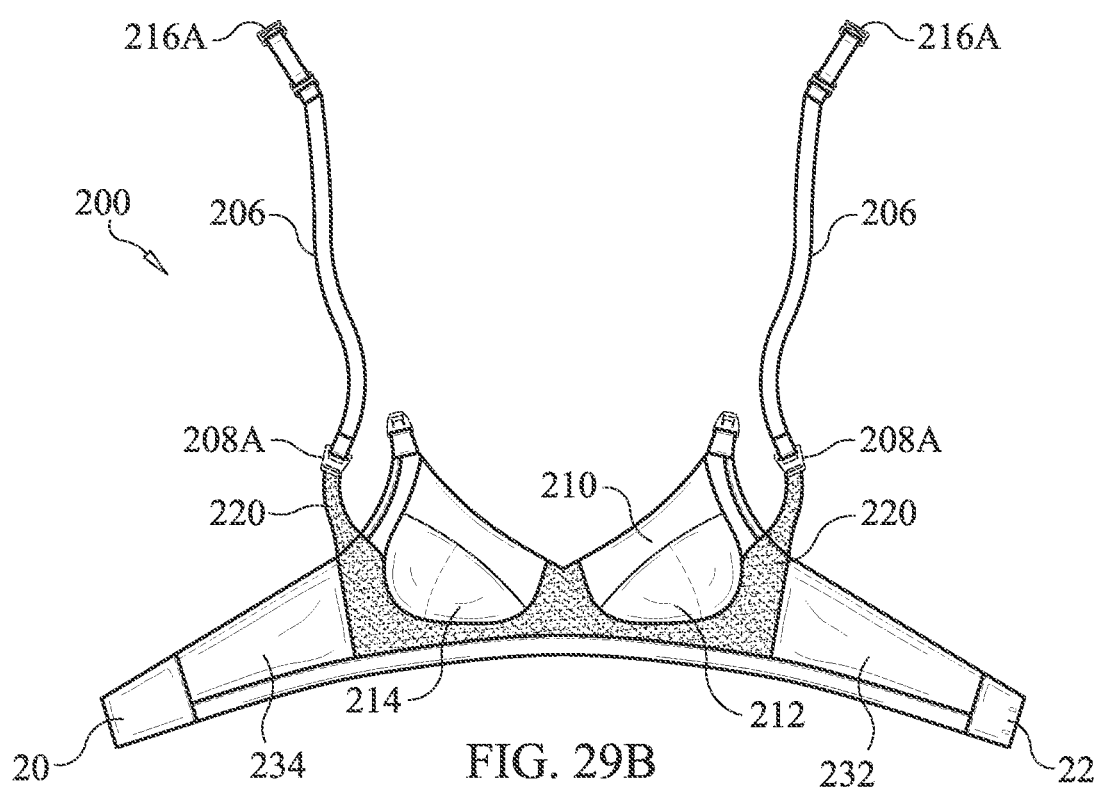
FIG. 29B is a rear view of the garment of FIG. 29A illustrating the disengagement mechanism in a disengaged position.

In some embodiments, as shown in FIG. 29A, the engagement mechanisms 208 include a first engagement member 208A that can be coupled to (or engage or attach to) a second engagement member 208B (FIGS. 29A and 29B illustrate the first and second engagement members decoupled or disengaged from each other). Engagement members 208A can be attached to the back panel as shown in FIGS. 29A and 29B. Engagement members 208B can be coupled to the center layer 210 as shown in FIG. 29A. The first and second engagement members 208A and 208B and/or an extension portion of back panels 220 may each be affixed to a shoulder strap 206 sized and shaped to enable a wearer to put on and take off garment 200 as well as provide support for the wearer's breasts and garment 200 when worn. Shoulder straps 206 can include a first fastening member 216A, which will be discussed in greater detail below with reference to FIGS. 31A-31D.

FIG. 29B illustrates a back or rear view of garment 200, which shows the extension portions of back panel 220 affixed to engagement members 208A when the engagement members 208A and 208B are not engaged together. When engagement members 208A and 208B are not engaged together, a portion of center layer 210, left inner layer 214, right inner layer 212, first panel 202, and/or second panel 204 may be decoupled from the back panel 220 as shown. In this way, when worn by the wearer, the decoupled engagement members 208A and a portion of garment 200 affixed thereto may be repositioned or moved so as to expose a portion of the wearer's underlying breast(s).

Figure 30A:
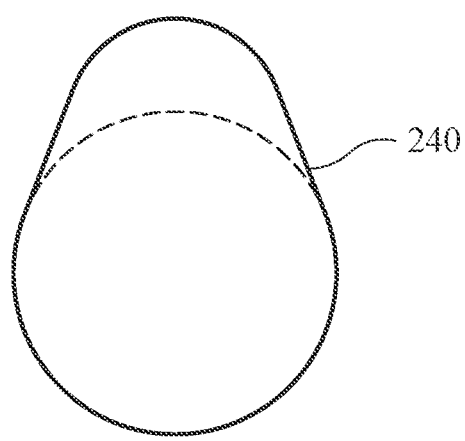
FIG. 30A is a front view of an optional breast pad of the garment of FIG. 28A.
Figure 30B:
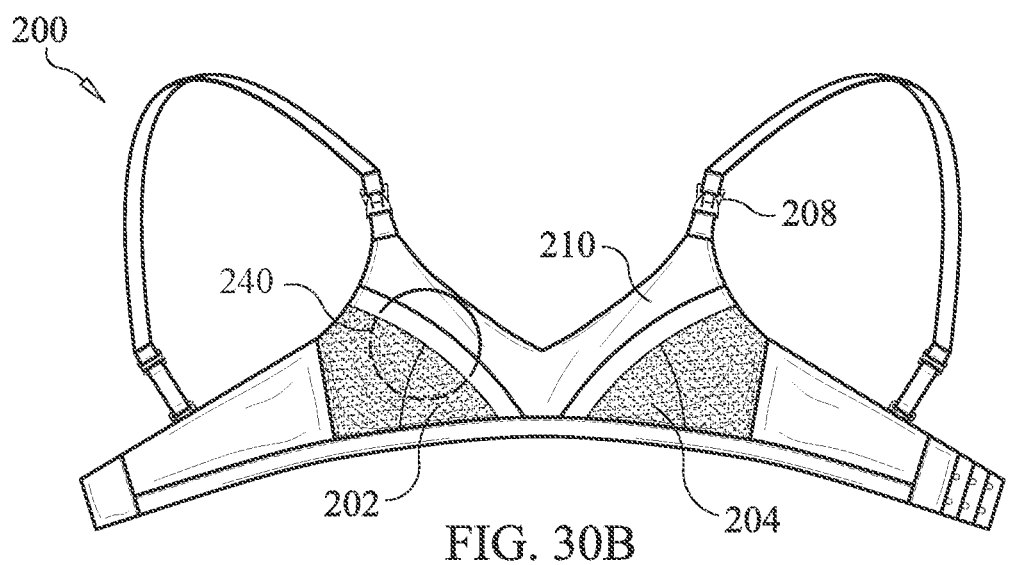
FIG. 30B is a front view of the garment of FIG. 28A illustrating the optional breast pad disposed therein at a first location.
Figure 30C:
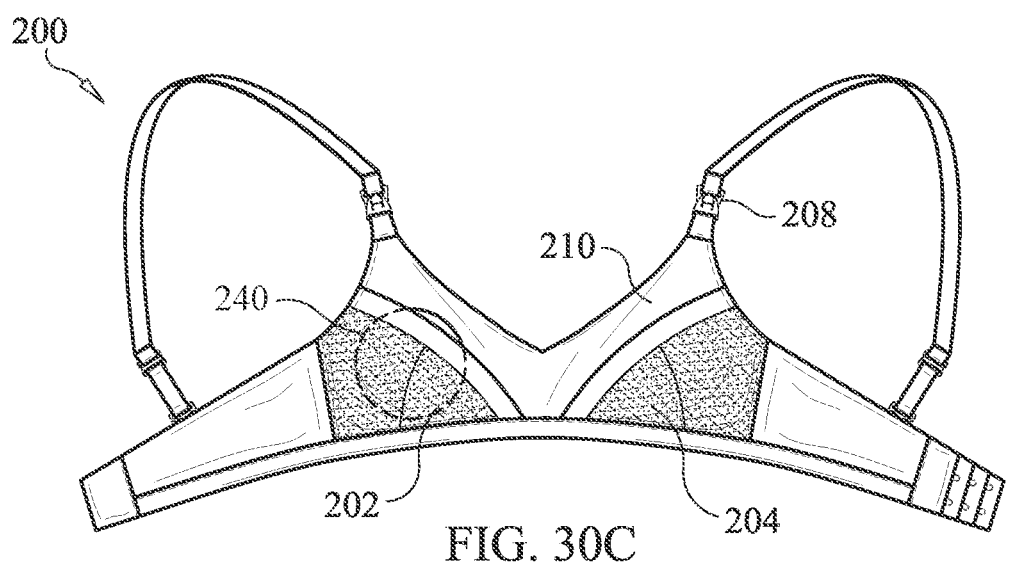
FIG. 30C is a front view of the garment of FIG. 28A illustrating the optional breast pad disposed therein at a second location.

FIG. 30A illustrates a breast pad 240 that can be removably inserted into garment 200 between a portion of first panel 202 and a portion of the right inner layer 212 and/or a portion of center layer 210 as shown in FIGS. 30B and 30C. Breast pad 240 may be manufactured from, for example, fabric, foam, rubber or some combination thereof. Breast pad 240 may be either disposable or reusable. When reusable, breast pads 240 may be manufactured so as to be machine or hand washable. In some embodiments, breast pad 240 may serve to smooth the exterior surface of garment 200, add volume to the garment 200, and/or protect an underlying breast or nipple of the wearer.

In another alternative embodiment, a garment (such as garment 200) can include a breast pad that is fixedly attached to a portion of the garment, i.e., not removable. For example, in such an embodiment, a breast pad can be coupled (e.g., sewn) to an inner surface of an outer panel (e.g., first panel 202 and/or second panel 204) of the garment.

Figure 31A:
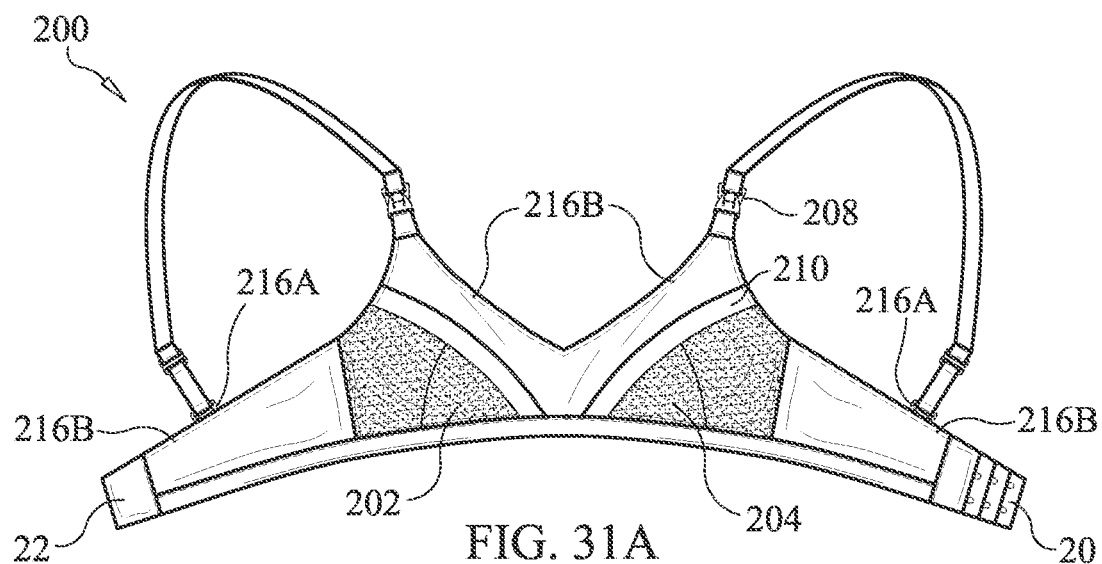
FIG. 31A is a front view of the garment of FIG. 28A illustrating openings defined along a perimeter top edge of the garment that can be used to couple straps thereto.
Figure 31B:
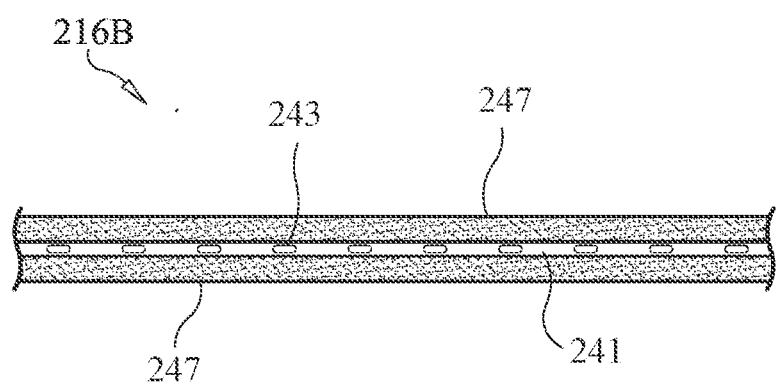
FIG. 31B is an enlarged view of the openings/holes defined along the perimeter top edge of the garment to which the straps of the garment of FIG. 28A can be secured.

FIGS. 31A-31D provide illustrations of how the shoulder straps 206 can be coupled to the garment 200. As described above, the straps 206 each include a first fastening member 216A coupled to an end thereof. To couple the strap 206 to the body of the garment 200, the first fastening members 216A can be coupled to a second fastening member 216B disposed along a upper/top perimeter portion of the body of the garment 200 as shown in FIG. 31A. As shown in FIG. 31B, the second fastening member 216B can include, for example, a length of fabric or elastic material 241 that defines multiple openings or holes 243 along a length thereof. In some embodiments, holes 243 may resemble button holes as shown in FIG. 31B. The length of fabric or elastic material 241 may be affixed to, or sewn into, a portion 247 (e.g., an upper edge) of garment 200. For example, in some embodiments, the length of fabric 241 can be disposed between the center layer 210 and the inner layers 212, 214 such that the holes 243 defined in the length of fabric 241 are visible along a top edge of the garment 200.

Figure 31C:
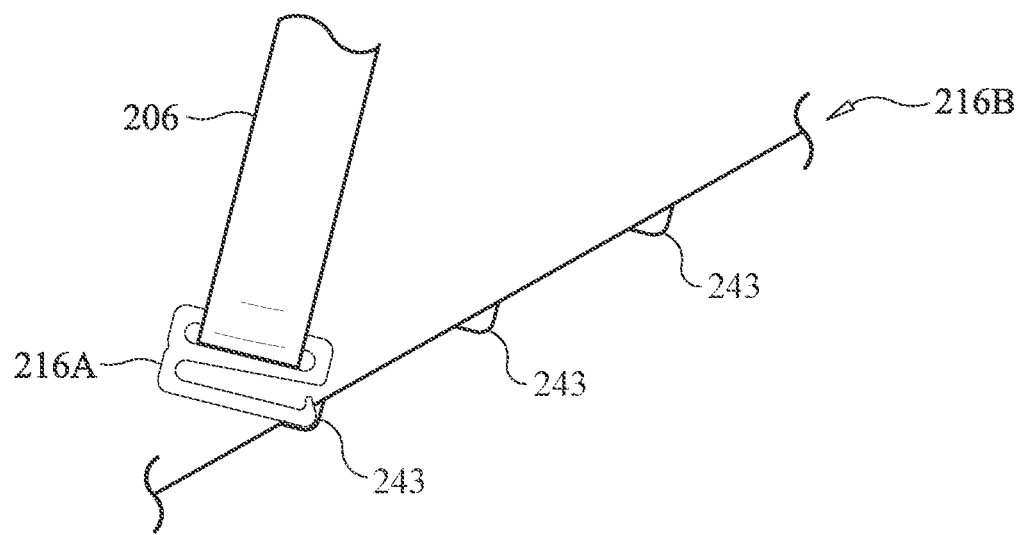
FIGS. 31C and 31D are each an enlarged view of a portion of the perimeter top edge of the garment of FIG. 31A illustrating the fastening mechanisms of the straps being inserted into the openings/holes defined therein.
Figure 31D:
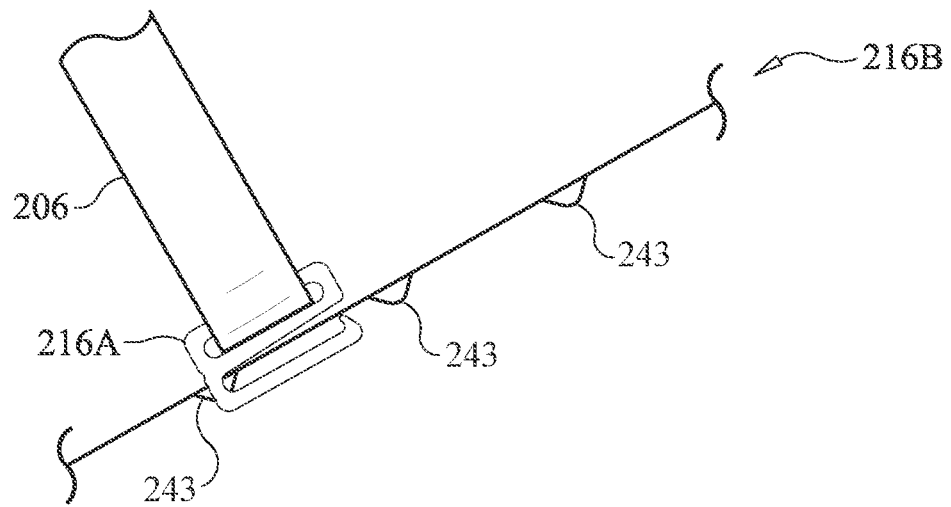

FIGS. 31C and 31D illustrate how a fastening member 216A affixed to a shoulder strap 206 can be releasably coupled to a selected hole 243 of the second fastening member 216B. As best shown in FIGS. 31C and 31D, first fastening member 216A may resemble a hook that can be inserted into a selected hole 243. The fastening member 216A can then be positioned within the hole 243 so as to be substantially parallel to a plane of the second fastening member 216B as fastened to garment 200 (see FIG. 31D). The first fastening member 216A may be securely and removably attached to a selected one of the holes 243 of fastening member 216B by virtue of its positioning or engagement within the hole 243 and/or via friction.

As shown in FIG. 31A, the garment 200 can include a fastening member 216B at multiple locations along an upper perimeter of the garment 200. For example, a first part of fastening member 216B can be disposed along a portion of the upper perimeter of garment 200 and a second part of fastening member 216B can be disposed along an outside perimeter of a portion of first wrap around panel 232 and second wrap around panel 234. A portion of the second part of the fastening member 216B may also be affixed to the upper perimeter of the center layer 210.

Figure 32A:
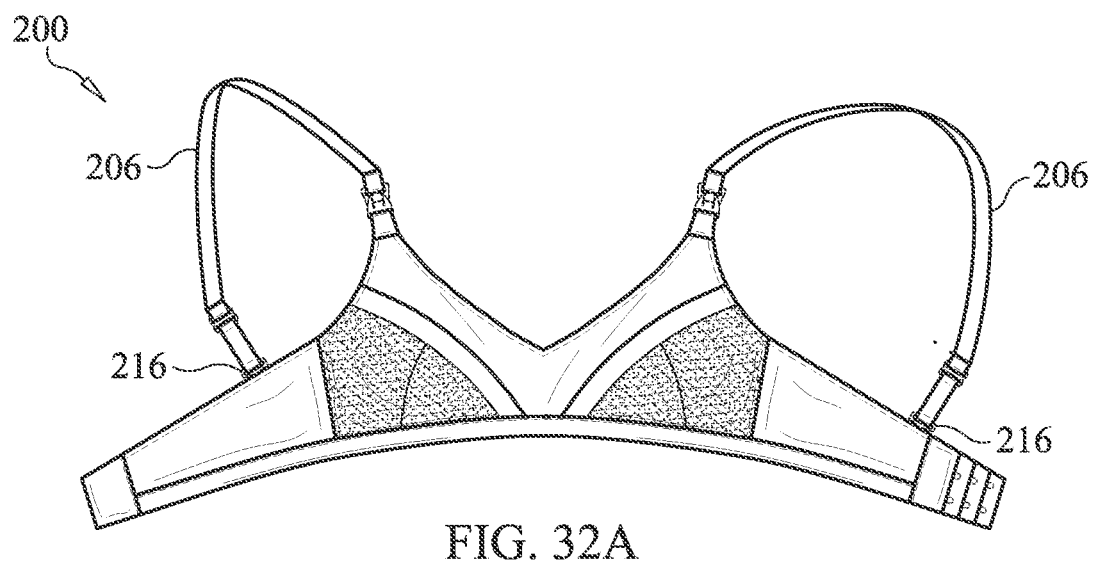
FIG. 32A is a front view of the garment of FIG. 28A illustrating a first fastening mechanism attached at a first location along a first wrap-around panel on a first side of the garment and a second fastening mechanism attached at a second location along a second wrap-around panel of the garment on a second side of the garment.

The multiple holes 243 of second fastening member 216B provide adjustability and allow a wearer to couple a strap 206 to the garment 200 at various different locations to, for example, improve the comfort of garment 200 when worn and/or provide support for breast weight, a portion of the breast pump, and/or a container of pumped breast milk, (e.g., such as pumping container 100) as may be used when expressing milk from a breast. For example, as shown in FIG. 32A, a wearer may couple the first fastening member 216A of a first shoulder strap 206 to a hole 243 of second fastening member 216B at a position on the second wrap around panel 234, and a second shoulder strap 206 with a first fastening member 216A can be coupled to a hole 243 of second fastening mechanism 216B at a position on the first wrap around panel 232 closer to the center layer 210 than the first shoulder strap 206. The adjustability of the attachment of the straps 206 to the body of the garment 200 allows a wearer to adjust the positioning of the straps 206 as desired.

Figure 32B:
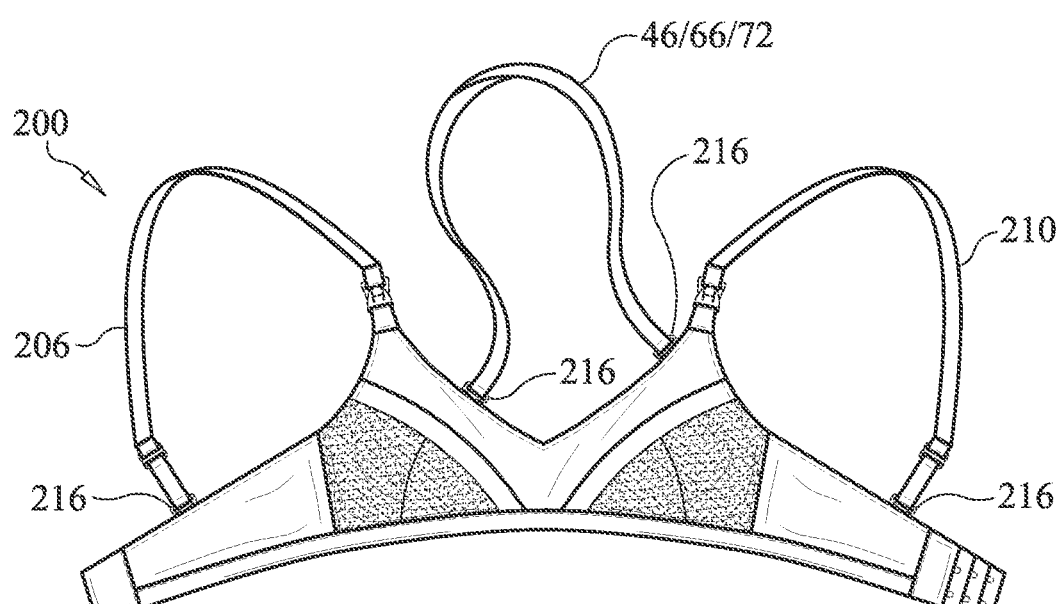
FIG. 32B is a front view of the garment of FIG. 32A illustrating an optional center or neck strap coupled to the perimeter top edge of the garment.

FIG. 32B shows garment 200 being used with a center strap 46/66/72, which may resemble neck strap 46, strap 66, and/or strap 72 (described above). In some embodiments a neck strap 46/66/72 can include a comfort portion that has a greater width as previously described above. Center strap 46/66/72 may include a first fastening member 216A, which may be engaged with any available hole 243 of second fastening member 216B. Often times, center strap 46/66/72 may be engaged with the portion of the second fastening member 216B positioned along or coupled to the upper perimeter of the center layer 210, as shown in FIG. 32B.

It will be appreciated that the configurations of the coupling of the first and second fastening members 216A and 216B are not limited by the examples provided by FIGS. 32A and 32B. For example, a wearer may crisscross the shoulder straps 206 such that the first fastening member 216A of the shoulder strap 206 on the right side of the garment 200 is coupled to the second fastening member 216B disposed on the wrap around panel 234 on the left side of the garment 200. Additionally, or alternatively, a wearer may position a first fastening member 216A of center strap 46/66/72 in any available hole 243 of second fastening member 216B.

Figure 33A:
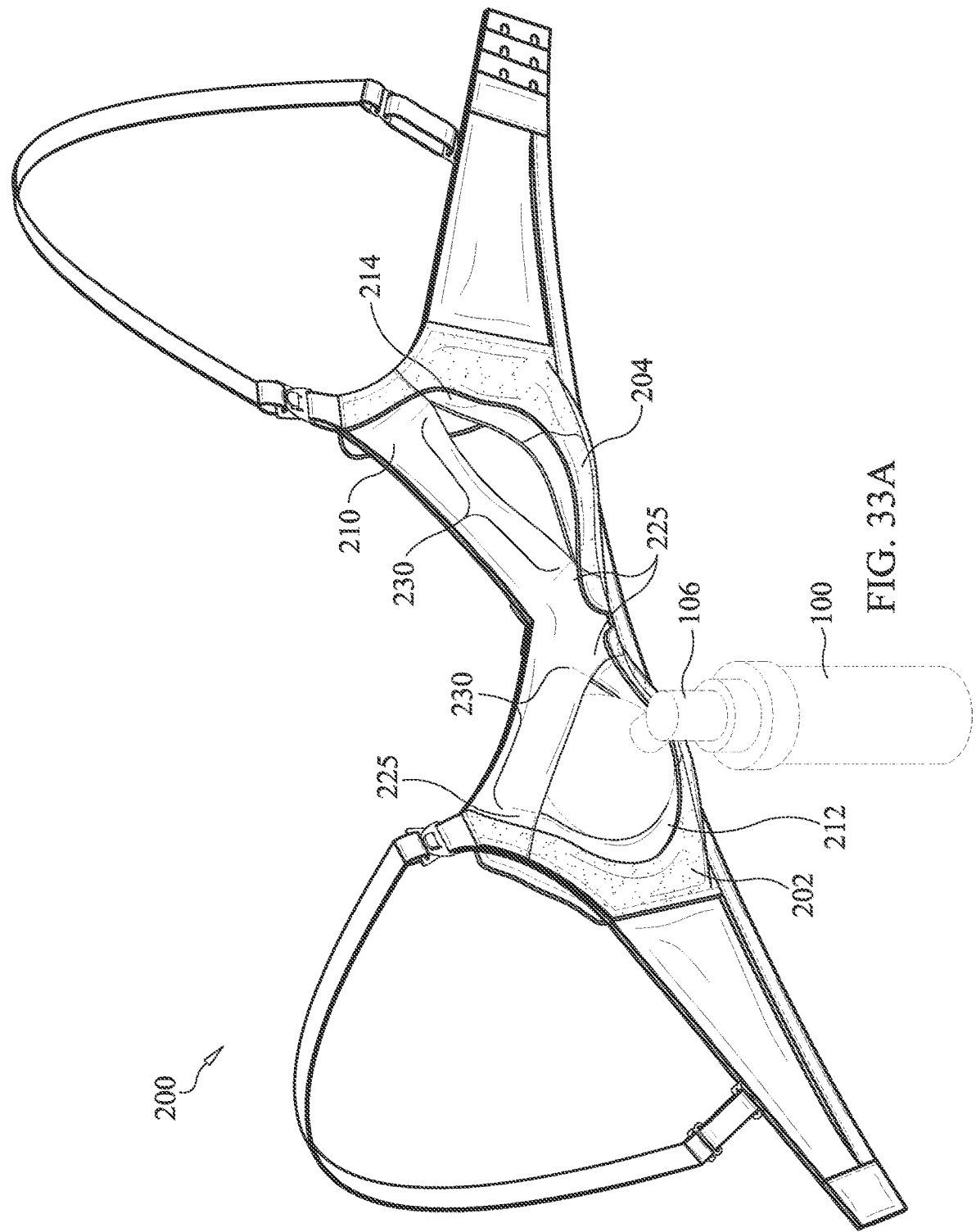
FIGS. 33A and 33B each depict the garment of FIG. 28A being used to support a breast pumping device.

FIG. 33A depicts the garment 200, showing second panel 204 and left inner layer 214, and/or a portion of center layer 210 are repositioned so as to expose opening 230. FIG. 33A also depicts a portion of first panel 202 pushed or moved downward so as to allow access to opening 230. Center layer 210 is separated from right inner layer 212 so as to provide a passageway for a portion of the breast pump (e.g., breast shield of breast pump body 106) through opening 230. In this fashion, the breast shield of breast pump body 106 may contact an underlying breast of a wearer so as to express and/or pump breast milk from the breast. Center layer 210, first panel 202, and/or right inner layer 212 may act to support a portion of the weight of the breast shield, the breast pump body 106 and/or expressed milk stored in pumping container 100, and/or assist in securing breast shield of breast pump body 106 against the wearer's breast.

Figure 33B:
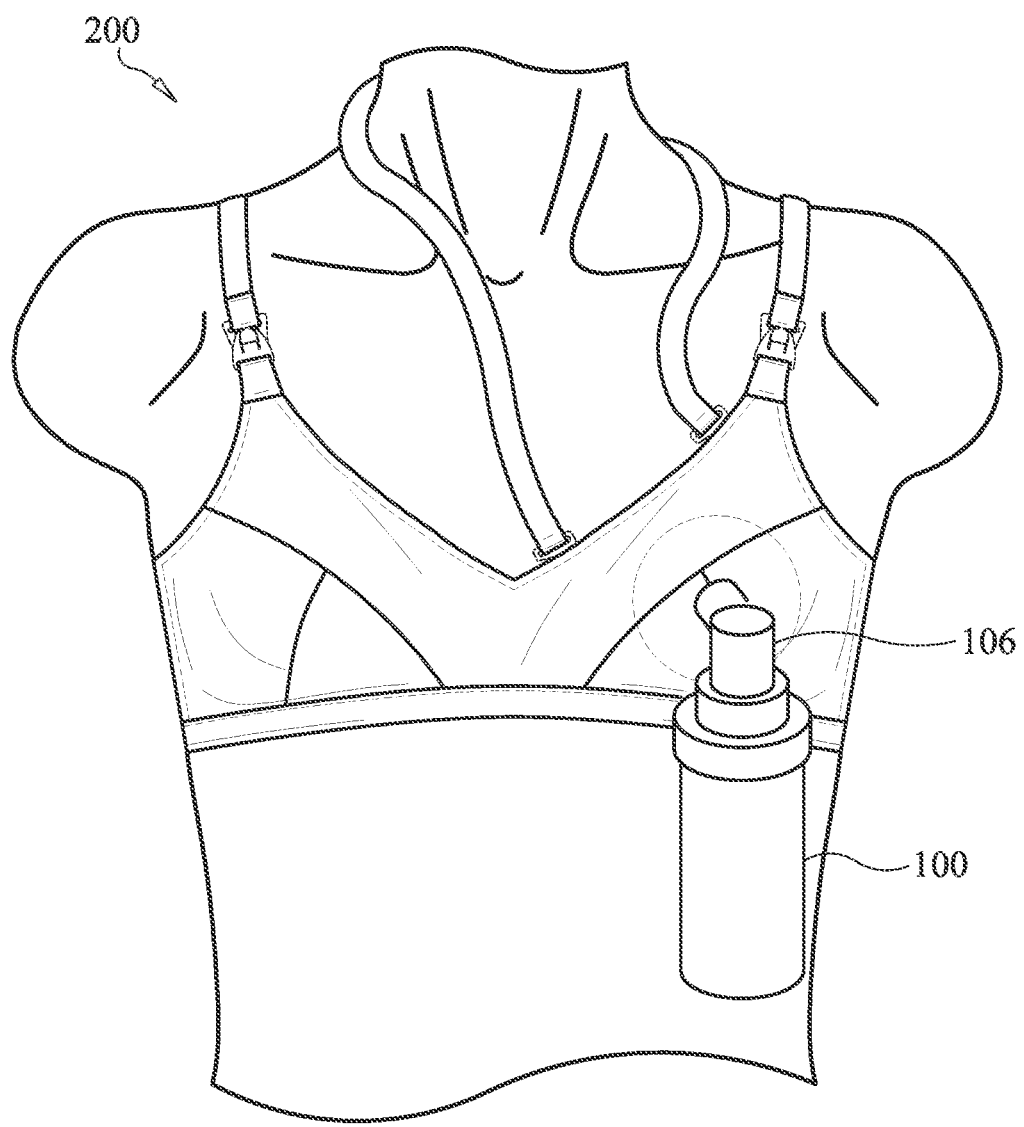

FIG. 33B depicts a wearer using a breast pump, or a portion thereof, on the first side (left side of wearer) while wearing garment 200 in a manner similar to that depicted in FIG. 33A.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. An apparatus, comprising:
an inner panel including a first portion of material coupled to a second portion of material such that the first portion of material and the second portion of material collectively define an opening configured to provide support for at least one of a wearer's breast or a portion of a breast pump inserted through the opening;
an outer panel coupled to the inner panel such that a portion of the outer panel overlaps the opening, a portion of the outer panel configured to be moved relative to the inner panel to expose the opening such that a portion of a breast pump can be inserted through the opening;
a back panel coupled to at least one of the inner panel and the outer panel, the back panel including an inner back panel layer, an outer back panel layer, and a length of material coupled between the inner back panel layer and the outer back panel layer, the length of material defining a plurality of openings disposed along a top edge portion of the back panel; and
a shoulder strap having a first end removably coupleable to the back panel via a select one of the plurality of openings, and a second end removably coupleable to the inner panel.

2. The apparatus of claim 1, wherein the opening defined by the first portion of material and the second portion of material of the inner panel is disposed at an oblique angle relative to a bottom edge of the inner panel.

3. The apparatus of claim 1, wherein the shoulder strap includes a hook disposed on the first end that is configured to be received within a select opening of the plurality of openings of the back panel to removably couple the shoulder strap to the back panel.

4. The apparatus of claim 1, further comprising:
a pad removably disposable between the inner panel and the outer panel.

5. The apparatus of claim 1, wherein at least a portion of the first portion of material overlaps at least a portion of the second portion of material at the opening.

6. The apparatus of claim 1, wherein an edge of the first portion of material and an edge of the second portion of material are aligned across the opening in an abutting relationship.

7. The apparatus of claim 1, wherein the inner panel is formed with a first material and the outer panel is formed with a second material different than the first material.

8. An apparatus, comprising:
an inner panel including a first portion of material coupled to a second portion of material such that the first portion of material and the second portion of material define an opening configured to provide support for at least one of a wearer's breast or a portion of a breast pump inserted through the opening, the second portion of material of the inner panel including an inner layer, an outer layer, and a length of material coupled between the inner layer and the outer layer, the length of material defining a plurality of attachment openings disposed along a top edge portion of the inner panel;
an outer panel coupled to the inner panel such that a portion of the outer panel overlaps the opening, a portion of the outer panel configured to be moved relative to the inner panel to expose the opening such that a portion of a breast pump can be inserted through the opening; and
a neck strap having a first end removably coupleable to a select first attachment opening from the plurality of attachment openings of the inner panel and a second end removably coupleable to a select second attachment opening from the plurality of attachment openings of the inner panel.

9. The apparatus of claim 8, wherein the opening defined by the first portion of material and the second portion of material of the inner panel is disposed at an oblique angle relative to a bottom edge of the inner panel.

10. The apparatus of claim 8, wherein the neck strap includes a first hook disposed on the first end configured to be received within a select first opening of the plurality of openings of the inner panel and a second hook disposed on the second end configured to be received within a select second opening of the plurality of openings of the inner panel to removably couple the neck strap to the inner panel.

11. The apparatus of claim 8, further comprising:
a pad removably disposable between the inner panel and the outer panel.

12. The apparatus of claim 8, wherein at least a portion of the first portion of material overlaps at least a portion of the second portion of material at the opening.

13. The apparatus of claim 8, wherein an edge of the first portion of material and an edge of the second portion of material are aligned across the opening in an abutting relationship.

14. The apparatus of claim 8, wherein the inner panel is formed with a first material and the outer panel is formed with a second material different than the first material.

15. The apparatus of claim 8, wherein the neck strap has a width that varies between the first end and the second end of the neck strap.

16. An apparatus, comprising:
an inner panel including a first portion of material coupled to a first portion of a center portion of material such that the first portion of material and the center portion of material define a first opening, and a second portion of material coupled to a second portion of the center portion of material such that the second portion of material and the center portion of material define a second opening, the first opening configured to provide support for at least one of a wearer's breast or a portion of a breast pump inserted through the first opening, the second opening configured to provide support for at least one of a wearer's breast or a portion of a breast pump inserted through the second opening;
a first outer panel coupled to at least one of the first portion of material of the inner panel or the center portion of material such that the first outer panel overlaps the first opening;
a second outer panel coupled to at least one of the second portion of material of the inner panel or the center portion of material such that the second outer panel overlaps the second opening,
a portion of the first outer panel configured to be moved relative to the inner panel to expose the first opening such that a portion of a breast pump can be inserted through the first opening,
a portion of the second outer panel configured to be moved relative to the inner panel to expose the second opening such that a portion of a breast pump can be inserted through the second opening; and
a neck strap having a first end coupleable to the inner panel at a first select location on the inner panel and a second end coupleable to the inner panel at a second location different than the first location on the inner panel.

17. The apparatus of claim 16, further comprising:
a first pad removably disposable between the inner panel and the first outer panel; and
a second pad removably disposable between the inner panel and the second outer panel.

18. The apparatus of claim 16, further comprising:
a first pad fixedly coupled to the first outer panel; and
a second pad fixedly coupled to the second outer panel.

19. The apparatus of claim 16, wherein at least a portion of the first portion of material overlaps at least a portion of the center portion of material at the first opening and at least a portion of the second portion of material overlaps at least a portion of the center portion of material at the second opening.

20. The apparatus of claim 16, wherein an edge of the first portion of material and an edge of the center portion of material are aligned across the first opening in an abutting relationship and an edge of the second portion of material and an edge of the center portion of material are aligned across the second opening in an abutting relationship.

21. The apparatus of claim 16, further comprising:
a back panel coupled to at least one of the inner panel and the outer panel, the back panel including a plurality of openings defined along a top edge portion of the back panel; and a shoulder strap having a first end removably coupleable to the back panel via a select one of the plurality of openings, and a second end removably coupleable to the inner panel.

22. An apparatus, comprising:
an inner panel including a first portion of material coupled to a second portion of material such that the first portion of material and the second portion of material define an opening configured to provide support for at least one of a wearer's breast or a portion of a breast pump inserted through the opening, the inner panel including a plurality of attachment openings defined along a top edge portion of the inner panel;
an outer panel coupled to the inner panel such that a portion of the outer panel overlaps the opening, a portion of the outer panel configured to be moved relative to the inner panel to expose the opening such that a portion of a breast pump can be inserted through the opening; and
a neck strap having a first end removably coupleable to a select first attachment opening from the plurality of attachment openings of the inner panel and a second end removably coupleable to a select second attachment opening from the plurality of attachment openings of the inner panel, the neck strap having a width that varies between the first end and the second end of the neck strap.

23. The apparatus of claim 22, wherein the second portion of material of the inner panel includes an inner layer, an outer layer and a length of material coupled between the inner layer and the outer layer, the length of material defining the plurality of attachment openings.

24. The apparatus of claim 22, wherein the opening defined by the first portion of material and the second portion of material of the inner panel is disposed at an oblique angle relative to a bottom edge of the inner panel.

25. The apparatus of claim 22, wherein the neck strap includes a first hook disposed on the first end configured to be received within a select first opening of the plurality of openings of the inner panel and a second hook disposed on the second end configured to be received within a select second opening of the plurality of openings of the inner panel to removably couple the neck strap to the inner panel.

26. The apparatus of claim 22, further comprising:
a pad removably disposable between the inner panel and the outer panel.

27. The apparatus of claim 22, wherein at least a portion of the first portion of material overlaps at least a portion of the second portion of material at the opening.

28. The apparatus of claim 22, wherein an edge of the first portion of material and an edge of the second portion of material are aligned across the opening in an abutting relationship.

29. The apparatus of claim 22, wherein the inner panel is formed with a first material and the outer panel is formed with a second material different than the first material.

30. An apparatus, comprising:
an inner panel including a first portion of material coupled to a first portion of a center portion of material such that the first portion of material and the center portion of material define a first opening, and a second portion of material coupled to a second portion of the center portion of material such that the second portion of material and the center portion of material define a second opening, the first opening configured to provide support for at least one of a wearer's breast or a portion of a breast pump inserted through the first opening, the second opening configured to provide support for at least one of a wearer's breast or a portion of a breast pump inserted through the second opening;
a first outer panel coupled to at least one of the first portion of material of the inner panel or the center portion of material such that the first outer panel overlaps the first opening;
a second outer panel coupled to at least one of the second portion of material of the inner panel or the center portion of material such that the second outer panel overlaps the second opening,
a portion of the first outer panel configured to be moved relative to the inner panel to expose the first opening such that a portion of a breast pump can be inserted through the first opening,
a portion of the second outer panel configured to be moved relative to the inner panel to expose the second opening such that a portion of a breast pump can be inserted through the second opening;
a back panel coupled to at least one of the inner panel and the outer panel, the back panel including a plurality of openings defined along a top edge portion of the back panel; and
a shoulder strap having a first end removably coupleable to the back panel via a select one of the plurality of openings, and a second end removably coupleable to the inner panel.

31. The apparatus of claim 30, further comprising:
a first pad removably disposable between the inner panel and the first outer panel; and
a second pad removably disposable between the inner panel and the second outer panel.

32. The apparatus of claim 30, further comprising:
a first pad fixedly coupled to the first outer panel; and
a second pad fixedly coupled to the second outer panel.

33. The apparatus of claim 30, wherein at least a portion of the first portion of material overlaps at least a portion of the center portion of material at the first opening and at least a portion of the second portion of material overlaps at least a portion of the center portion of material at the second opening.

34. The apparatus of claim 30, wherein an edge of the first portion of material and an edge of the center portion of material are aligned across the first opening in an abutting relationship and an edge of the second portion of material and an edge of the center portion of material are aligned across the second opening in an abutting relationship.

35. The apparatus of claim 30, further comprising:
a neck strap having a first end coupleable to the inner panel at a first select location on the inner panel and a second end coupleable to the inner panel at a second location different than the first location on the inner panel.

* * * * *